United States Patent [19]

Britcher et al.

[11] Patent Number: 5,171,860

[45] Date of Patent: Dec. 15, 1992

[54] DIAMINO ISOTHIAZOLE-1-OXIDES AND 1,1 DIOXIDES AS GASTRIC SECRETION INHIBITORS

[75] Inventors: Susan F. Britcher, Norristown; William C. Lumma, Jr., Pennsburg, both of Pa.

[73] Assignee: Merck & Co., Inc., Rahway, N.J.

[21] Appl. No.: 794,339

[22] Filed: Nov. 12, 1991

Related U.S. Application Data

[63] Continuation of Ser. No. 537,203, Jun. 12, 1990, abandoned, which is a continuation of Ser. No. 318,489, Mar. 2, 1989, abandoned, which is a continuation of Ser. No. 774,630, Sep. 11, 1985, abandoned, which is a continuation of Ser. No. 378,411, May 17, 1982, abandoned, which is a continuation-in-part of Ser. No. 273,682, Jun. 15, 1981, abandoned.

[51] Int. Cl.$^5$ .................. C07D 275/02; A61K 31/41
[52] U.S. Cl. ...................................... 548/107; 546/209
[58] Field of Search ................ 548/107; 514/372, 326; 546/209

[56] References Cited

U.S. PATENT DOCUMENTS

| | | | |
|---|---|---|---|
| 3,950,333 | 10/1975 | Durant et al. | 548/107 |
| 4,128,658 | 4/1976 | Price et al. | 548/107 |
| 4,394,508 | 7/1983 | Crenshaw et al. | 546/209 |

FOREIGN PATENT DOCUMENTS 55-53288  4/1980  Japan .

Primary Examiner—David B. Springer
Attorney, Agent, or Firm—Mark R. Daniel; Joseph F. DiPrima

[57] ABSTRACT

This invention is directed to diamino isothiazole -1-oxides and -1,1-dioxides and related compounds as well as pharmaceutical compositions and methods useful in the treatment of gastric secretion in mammals.

32 Claims, No Drawings

DIAMINO ISOTHIAZOLE-1-OXIDES AND 1,1 DIOXIDES AS GASTRIC SECRETION INHIBITORS

This application is a continuation of Ser. No. 07/537,203, filed on Jun. 12, 1990, which is a continuation of Ser. No. 07/318,489, filed on Mar. 2, 1989, which is a continuation of Ser. No. 06/774,630, filed on Sep. 11, 1985, which is a continuation of Ser. No. 06/378,411, filed on May 17, 1982, which is a continuation-in-part of Ser. No. 06/273,682, filed on Jun. 15, 1981, all of which are now abandoned.

BACKGROUND OF THE INVENTION

Inhibitors of gastric acid secretion functioning by antagonism of the histamine H2-receptor are effective antiulcer agents. Structurally, such compounds are typically viewed as molecules having three substituents or fragments; i.e., A-B-C, each of which can independently affect the antisecretory activity. The "A" portion may be a substituted or unsubstituted aromatic or heteroaromatic group such as are disclosed in, for example, U.S. Pat. No. 3,950,333 to Durant et. al., U.S. Pat. No. 4,128,658 to Price et. al., and Belgian Patents 867,106 and 875,846 (Derwent Abstracts 84065A/47 and 79110B/44, respectively).

The central, or "B" portion, may be a connecting chain joined to A such as A—$CH_2SCH_2CH_2$—, $AOCH_2CH_2CH_2$, and the like.

The remaining terminal substituent "C" is structurally distinct from either the A or B portions and may be, for example, a substituted guanidine, a substituted 1,1-diamino ethylene, or a 3,5-diamino-1-alkyl triazole as disclosed in the aforementioned U.S. Patents to Durant et. al., and Price et. al., as well as in Belgian Patent 875,846.

The present invention is directed to unique "C" moieties which confer antisecretory activity when combined with the A-B molecular fragments comprising these antiulcer agents. These novel "C" moieties, i.e., 3,4-diaminoisothiazole-1-oxides and -1,1-dioxides, when incorporated into the A-B molecular fragments, afford compounds that exhibit gastric antisecretory activity comparable to or greater than known prior art compounds, including those disclosed in the above-identified U.S., Belgian and European patents. The disclosure of 4-isothiazolin-3-one-1-oxides and -1,1-dioxides in U.S. Pat. No. 4,062,859 does not teach or suggest how to synthesize the novel compounds of this invention as no appropriate precursors nor amine displacement reactions are disclosed.

SUMMARY OF THE INVENTION

This invention is directed to diamino isothiazole -1-oxides and 1,1-dioxides and related compounds as well as processes for the preparation of such compounds.

DESCRIPTION OF THE INVENTION

The compounds of this invention are represented by the following structural formulae:

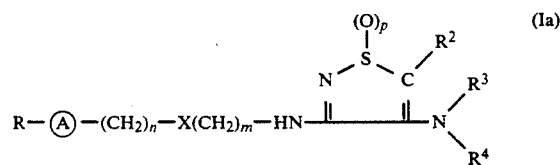

and

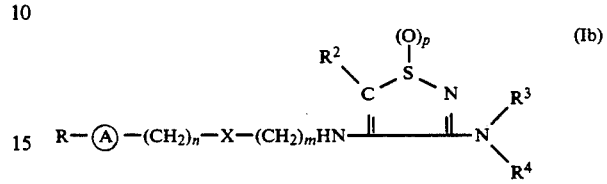

wherein in both of the above structural formulae:
R is hydrogen, loweralkyl,

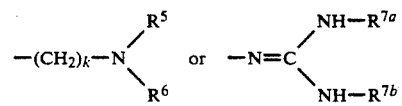

wherein
$R^5$ and $R^6$ are independently hydrogen, loweralkyl, cycloloweralkyl or phenylloweralkyl or $R^5$ and $R^6$ may be joined to from, along with the nitrogen to which the are attached, a 5- or 6-membered heterocycle, which may also contain an oxygen, sulfur, SO, $SO_2$, or an N—$R^8$ linkage wherein $R^8$ is hydrogen, loweralkyl of from 1 to 3 carbon atoms, loweralkenyl, or loweralkynyl;

$R^{7a}$ and $R^{7b}$ are independently hydrogen, or loweralkyl, 3,3,3-trifluoroethyl or $R^{7a}$ and $R^{7b}$ may be joined together to form a cyclic structure through an —$(CH_2)_k$-linkage;

p is 1 or 2;
n is 0 or 1;
m is 2 to 4;
k is 0 to 4;
X is oxygen, sulfur or methylene:
$R^2$ is hydrogen; halogen; loweralkyl; loweralkoxy; aryl; substituted aryl wherein the substituents are loweralkyl, halogen, loweralkoxy, trifluoromethylthio, and trifluoromethylsulfonyl; $CH_2OH$; CN; $CONR^{7a}R^3$; $SO_2NR^3R^{7a}$; wherein $R^{7a}$ is as defined above and $R^3$ is as defined below; or $COR^9$; $CO_2R^9$; $CONR^3R^9$; and $SO_2R^9$ wherein $R^9$ can be hydrogen, loweralkyl, substituted loweralkyl wherein the substituent is hydroxy, loweralkoxy, $NHCOR^{7a}$ wherein $R^{7a}$ is as defined above; aryl, substituted aryl, and, arylloweralkyl;

$R^3$ and $R^4$ are independently hydrogen, loweralkyl, loweralkenyl, loweralkynyl, cycloloweralkyl, phenyl, pyridyl, or substituted loweralkyl or substituted loweralkynyl wherein the alkyl and alkynyl substituents are phenyl, substituted phenyl, cycloloweralkyl, pyridyl, imidazolyl, morpholino, hydroxy, loweralkoxy, loweralkylthio; di(loweralkyl)amino, or $NCOR^3R^{7a}$ or $R^3$ and $R^4$ may be joined to form, along with the nitrogen to which they are attached, a 5- or 6-membered heterocycle which may also contain an oxygen, sulfur, SO, $SO_2$, N—$R^8$, or an $NOR^8$ linkage wherein $R^8$ is as defined above;

Ⓐ is phenylene or a 5- or 6-membered heterocycle containing one to three heteroatoms selected from oxygen, sulfur or nitrogen, which may optionally have a benzo ring fused thereon; and, a substituted 5-membered heterocycle wherein the substituents are loweralkyl, lower alkoxy carbonyl, halo, carbamoyl, substituted carbamoyl;

provided that when Ⓐ in Formulae Ia and Ib above is a 5-membered heterocycle, or a benzo fused 5-membered heterocycle containing one heteroatom, n is 1; and, the physiologically acceptable salts and N-oxides thereof.

Examples of Ⓐ in Formulae Ia or Ib are furan, thiophene, pyrrole, oxazole, oxadiazole, thiadiazole, thiazole, triazol, pyrazole, imidazole, pyridine, pyrimidine, pyrazine, and the like and the fused benzo derivatives thereof such as benzofuran, benzoxazole, benzimidazole, and the like.

It is further provided that when RⒶ in either Formulae Ia or Ib is a furan or a thiazole having the structures:

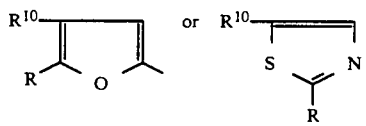

then R is as defined above and $R^{10}$ is loweralkyl, hydroxyloweralkyl, alkoxyalkyl, alkoxycarbonyl, $O=CNR^3R^{7a}$ wherein $R^3$ and $R^{7a}$ are as defined above; halo, preferably chlorine or bromine, or aryl, preferably phenyl.

Examples of the 5- or 6-membered heterocycles represented by $R^3$ and $R^4$ when joined and by $R^5$ and $R^6$ when joined are pyrrolidino, piperidino, morpholino, thiomorpholino, piperazino, and N-loweralkyl piperazino.

In the instant invention, unless specified otherwise, the term "loweralkyl" is intended to include those alkyl groups containing from 1 to 5 carbon atoms in either a straight or branched configuration. Examples of such alkyl groups are methyl, ethyl, propyl, iso-propyl, butyl, sec-butyl, pentyl and the like.

The term "cycloloweralkyl" is intended to include those cycloalkyl groups of from 3 to 7 carbon atoms. Examples of such cycloalkyl groups are cyclopropyl, cyclobutyl, cyclopentyl, cyclohexyl, and cycloheptyl.

The term "loweralkenyl" is intended to include those alkenyl groups of from 3 to 7 carbon atoms of either a straight or branched configuration. Examples of such alkenyl groups are propenyl, butenyl, pentenyl, and the like.

The term "loweralkynyl" is intended to include those alkynyl groups of from 3 to 7 carbon atoms of either a straight or branched configuration. Examples of such alkynyl groups are propargyl, butynyl, pentynyl, and the like.

The terms "alkoxyalkyl", "hydroxyalkyl" and "alkoxycarbonyl" are intended to include those normal and branched alkyl groups containing from 1 to 5 carbon atoms. Thus, the term "alkoxyalkyl" is exemplified by such compounds as methoxymethyl, ethoxy methyl, methoxy propyl, methoxy butyl, and the like; the term "hydroxyalkyl" is exemplified by such substituents as hydroxy methyl, hydroxy ethyl, hydroxypropyl, hydroxybutyl, and the like; and, the term "alkoxycarbonyl" is exemplified by such compounds as methoxycarbonyl, ethoxycarbonyl, propoxycarbonyl, butoxycarbonyl, and the like. The preferred compounds of the instant invention will have definitions which vary with the nature of the compounds of Formulae Ia and Ib.

Compounds Ia are the preferred compounds of this invention.

Preferred Ia compounds of the invention are realized when $R^3$ and $R^4$ are independently hydrogen, loweralkyl, loweralkynyl, substituted loweralkyl, or substituted loweralkynyl wherein the substituents in the alkyl and alkynyl groups are loweralkoxy, phenyl, pyridyl or imidazolyl; and $R^5$ and $R^6$ are independently hydrogen, loweralkyl, cycloloweralkyl or when $R^5$ and $R^6$ are joined to form a piperidine heterocyclic ring.

Further such preferred compounds are those wherein Ⓐ is m-phenylene or a 6-membered heterocycle as defined above, n is O, D X is oxygen, m is 3 and R is:

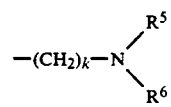

In such cases it is further preferred that k be 1 and $R^5$ and $R^6$ be loweralkyl, preferably methyl, or joined to form a morpholine, thiomorpholine, thiomorpholine S-oxide, thiomorpholine S-dioxide, piperidine or N-loweralkyl piperazine, heterocyclic ring.

Additional preferred variations of Ⓐ are those wherein Ⓐ is furan, imidazole, thiazole, oxazole, thiophene, triazole, thiadiazole, oxadiazole or benzofuran.

When Ⓐ is heterocyclic containing one heteroatom, it is preferred that n=1, X=sulfur and m=2.

Preferred variations of $R^2$ are carboxy, loweralkoxycarbonyl, benzyloxycarbonyl, carbamoyl, substituted carbamoyl, cyano, sulfamoyl, phenyl, and loweralkyl.

The preferred values of R will depend upon and vary with the definition of Ⓐ. When Ⓐ is furan or benzofuran, R is preferred to be:

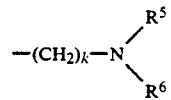

wherein it is further preferred that k=1 and $R^5$ and $R^6$ be hydrogen or loweralkyl, preferably hydrogen or methyl, or joined to form a morpholine, thiomorpholine, piperidine, or N-methyl piperazine ring.

When Ⓐ is thiazolyl, R is preferably

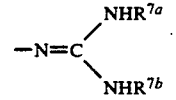

wherein $R^{7a,7b}$ are most preferably hydrogen.

The preferred compounds of the invention described above also include the physiologically acceptable salts and the N- and S-oxides thereof.

Examples of the compounds of this invention are:

(1)  3-N-[2-[4-methyl-5-imidazolyl)methylthio]ethyl-]amino-4-methylamino-5-methoxycarbonyl-isothiazole-1,1-dioxide (2)  3-N-[2-[(5-dimethylaminomethyl-2-furanyl)methylthio]ethyl]amino-4-propynylamino-5-carbamoylisothiazole-1,1-dioxide (3) 3-N-[2-[(2-guanidino-4-thiazolyl)methylthiolethyl]amino-4-amino-5-(N-methylcarbamoyl)-isothiazole-1,1-dioxide
(4) 3-N-[3-[3-(dimethylaminomethyl)phenoxy]propyl]amino-4-methylamino-5-cyanoisothiazole-1,1-dioxide
(5) 3-N-[2-[(4-methyl-5-imidazolyl)methylthio]ethyl]amino-4-amino-5-(ethoxycarbonyl)-isothiazole-1,1-dioxide
(6) 3-N-[2-[(5-dimethylaminomethyl-2-furanyl)methylthio]ethyl]amino-4-amino-5-benzyloxycarbonylisothiazole-1,1-dioxide
(7) 3-N-[2-[(2-guanidino-4-thiazolyl)methylthio]ethyl]amino-4-dimethylamino-5-carbamoylisothiazole-1,1-dioxide
(8) 3-N-[3-[3-(dimethylaminomethyl)phenoxy]propyl]amino-4-(2-methoxyethyl)amino-5-ethoxycarbonylisothiazole-1,1-dioxide
(9) 3-N-[2-[(4-methyl-5-imidazolyl)methylthio]ethyl]amino-4-(2-pyridylethyl)amino-5-ethoxycarbonylisothiazole-1,1-dioxide
(10) 3-N-[2-[(5-dimethylaminomethyl-2-furanyl)methylthio]ethyl]amino-4-amino-5-sulfamoylisothiazole-1,1-dioxide
(11) 3-N-[2-[(2-guanidino-4-thiazolyl)methylthio]ethyl]amino-4-methylamino--5-(N-methylsulfamoyl)isothiazole-1,1-dioxide
(12) 3-N-[3-[3-(dimethylaminomethyl)phenoxy]propyl]amino-4-amino-5-(N,N-dimethylsulfamoyl)isothiazole-1,1-dioxide
(13) 3-N-[2-[(4-methyl-5-imidazolyl)methylthio[ethyl]-amino-4-amino-5-carbamoylisothiazole-1,1dioxide
(14) 3-N-[2-[(5-dimethylaminomethyl-2-furanyl)methylthio]ethyl]amino-4-amino-5-benzoylisothiazole-1,1-dioxide
(15) 3-N-[2-[(2-guanidino-4-thiazolyl)-methylthio]ethyl]amino-4-methylamino-5-acetylisothiazole-1,1-dioxide
(16) 3-N-[3-[3-(dimethylaminomethyl)phenoxy]propyl]amino-4-amino-5-acetylisothiazole]-1,1-dioxide
(17) 3-N-[2-[(5-dimethylaminomethyl-2-furanyl)methylthio]ethyl]amino-4-amino-5-ethoxycarbonylisothiazole-1,1-dioxide
(18) 3-N-[3-[3-(1-piperidinylmethyl)phenoxy]propyl]amino-4-amino-5-ethoxycarbonylisothiazole-1,1-dioxide
(19) 3-N-[3-[3-(dimethylaminomethyl)phenoxy]-propylamino-4-amino-5-sulfamoylisothiazole-1,1-dioxide
(20) 3-N-[2-[(5-dimethylaminomethyl-2-furanyl)methylthio]ethyl]amino-4-amino-5-cyanoisothiazole-1,1dioxide
(21) 3-N-[3-[3-(cyclopropylaminomethyl)phenoxy]-propyl]amino-4-amino-5-carbamoylisothiazole-1,1dioxide
(22) 3-N-[2-[[6-(4-morpholinylmethyl)-2-benzofuranyl]methylthio]ethyl]amino-4-amino-5-carboxy isothiazole-1,1-dioxide
(23) 3-N-[3-[3-(dimethylaminomethyl)phenoxy]propyl]amino-4-amino-5-carboxyisothiazole-1,1-dioxide
(24) 3-N-[2-[(5-dimethylaminomethyl-2-furanyl)methylthio]ethyl]amino-4-amino-5-N-[(2-dimethylamino)ethyl]carbamoylisothiazole-1,1-dioxide
(25) 3-N-[2-[(4-methyl-5-oxazolyl)methylthio]ethylamino-4-amino-5-N-(2-hydroxyethyl)carbamoylisothiazole-1,1-dioxide
(26) 3-N-[2-[[6-(4-morpholinylmethyl)-2-benzofuranyl]methylthio]ethyl [amino-4-amino-5-N-(2-hydroxyethyl)carbamoylisothiazole-1,1-dioxide
(27) 3-N-[2-(5-dimethylaminomethyl-2-furanyl)methylthio]ethyl]amino-4-amino-5-methylisothiazole-1,1-dioxide
(28) 3-N-[2-[(2-guanidino-4-thiazolyl)methylthio[ethyl]amino-4-amino-5-methylisothiazole-1,1-dioxide
(29) 3-N-[2-[(2-guanidino-5-methyl-4-thiazolyl)methylthio]ethyl]amino-4-amino-5-ethoxycarbonylisothiazole-1,1-dioxide
(30) 3-N-[2-[(4-methyl-5-imidazolyl)methylthio]ethyl]amino-4-methylaminoisothiazole-1-oxide
(31) 3-N-[2-[(5-dimethylaminomethyl-2-furanyl)methylthio]ethyl]amino-4-methylamino-5-ethoxycarbonylisothiazole-1,1-dioxide
(32) 3-N-[2-[(2-guanidino-4-thiazolyl)methylthio]ethyl]amino-4-methylamino-5-carbamoylisothiazole-1-oxide
(33) 3-N-[3-[3-(dimethylaminomethyl)phenoxy]propyl]amino-4-amino-5-ethoxycarbonyl-isothiazole-1-oxide
(34) 3-N-[3-[3-(1-piperidinylmethyl)phenoxy]propyl]amino-4-amino-5-carbamoylisothiazole-1-oxide
(35) 3-N-[2-[(5-methylaminomethyl-2-furanyl)methylthio]ethyl]amino-4-amino-5-sulfamoylisothiazole-1-oxide
(36) 3-N-[2-(4-methyl-5-imidazolyl)methylthio]ethyl]amino-4-amino-5-carboxyisothiazole-1-oxide
(37) 3-N-[2-[(2-guanidino-4-thiazolyl)methylthio]ethyl]amino-4-methylamino-5-(N-methylcarbamoyl)isothiazole-1-oxide
(38) 3-N-[3-[3-(dimethylaminomethyl)phenoxy]propyl]amino-4-amino-5-(N-methylsulfamoyl)isothiazole-1-oxide
(39) 3-N-[2-[(5-dimethylaminomethyl-2-thienyl)methylthio]ethyl]amino-4-amino-5-cyanoisothiazole-1-oxide
(40) 3-N-[2-(2-pyridylmethylthio)ethyl]amino-4-amino-5-ethoxycarbonylisothiazole-1-oxide
(41) 3-N-[2-[(5-dimethylaminomethyl-2-thienyl)methylthio]ethyl]amino-4-methylamino-5-carbamoylisothiazole-1,1-dioxide
(42) 3-N-[2-(2-pyridylmethylthio)ethyl]amino-4-amino-5-carbamoylisothiazole-1,1-dioxide
(43) 3-N-[2-[(2-dimethylaminomethyl-5-thiazolyl)methyl-thio]ethyl]amino-4-amino-5-ethoxycarbonyl isothiazole-1,1-dioxide
(44) 3-N-[3-[4-(4-methylpiperazinyl)-3-thiadiazolyloxy]propyl]amino-4-amino-5-ethoxycarbonyl-isothiazole-1,1-dioxide
(45) 3-N-[3-[3-(1-piperidinylmethyl)phenoxy]propyl]amino-4-amino-5-benzyloxycarbonylisothiazole1,1-dioxide
(46) 3-N-[2-[(2-guanidino-4-thiazolyl)methylthio]ethyl]amino-4-amino-5-ethoxycarbonylisothiazole-1,1-dioxide
(47) 3-N-[3-[5-(dimethylaminomethyl)-2-oxazolyloxy]propyl]amino-4-(3-propynyl)amino-5-ethoxycarbonylisothiazole-1,1-dioxide
(48) 3-N-[2-[(5-dimethylaminomethyl-2-furanyl)methylthio]ethyl]amino-4-amino-5-methanesulfonylisothiazole-1-oxide
(49) 3-N-[2-[(5-dimethylaminomethyl-2-furanyl)methylthio]ethyl]amino-4-amino-5-methanesulfonylisothiazole-1,1-dioxide
(50) 4-N-[2-[(5-dimethylaminomethyl-2-furanyl)methylthio]ethyl]amino-3-amino-5-carbamoylisothiazole-1-oxide

(51) 4-N-[2-[(5-dimethylaminomethyl-2-furanyl)methylthio]ethyl]amino-3-amino-5-carbamoylisothiazole1,1-dioxide

(52) 3-N-[2-[(3-dimethylaminomethyl-2-furanyl)methylthio]ethyl]amino-4-amino-5-ethoxycarbonylisothiazole-1-oxide

(53) 3-N-[2-[(5-dimethylaminomethyl-2-furanyl)methylthio]ethyl]amino-4-amino-5-carboxyisothiazole-1-oxide

(54) 3-N-[2-[(5-dimethylaminomethyl-2-furanyl)methylthio]ethyl]amino-4-amino-5-carboxyisothiazole1,1-dioxide

(55) 3-N-[2-[5-(dimethylaminomethyl-2-furanyl)methylthio]ethyl]amino-4-methylthio-5-ethoxycarbonylisothiazole-1,1-dioxide

(56) 3-N-[2-[5-(dimethylaminomethyl-2-furanyl)methylthio]ethyl]amino-4-amino-5-benzyloxycarbonylisothiazole-1-oxide

(57) 3-N-[2-[5-(dimethylaminomethyl-2-furanyl)methylthio]ethyl]amino-4-amino-5-N,N-dimethylcarbamoylisothiazole-1,1-dioxide

(58) 3-N-[2-[5-(dimethylaminomethyl-2-furanyl)methylthio]ethyl]amino-4-amino-5-(2-hydroxyethoxy)carbonylisothiazole-1,1-dioxide

(59) 3-N-[2-[5-(dimethylaminomethyl-2-furanyl)methylthio]ethyl]amino-4-amino-5-(2-acetamidoethoxy)carbonylisothiazole-1,1-dioxide

(60) 3-N-[2-[2-guanidino-5-chloro-4-thiazole)methyl thio]ethyl]amino-4-amino-5-ethoxycarbonylisothiazole-1,1-dioxide

(61) 3-N-[2-[5-(dimethylaminomethyl-2-furanyl)methylthio]ethyl]amino-4-amino-5-t-butyloxycarbonylisothiazole-1,1-dioxide.

The compounds according to the invention readily form physiologically acceptable salts. Such salts include salts with inorganic acids such as hydrochlorides, hydrobromides, sulfates, nitrates and phosphates. Particularly useful salts of organic acids are formed with aliphatic mono- or dicarboxylic or sulfonic acids. Examples of such salts are acetates, maleates, fumarates, tartrates, citrates, benzoates, succinates, methane sulfonates, and isethionates. The compounds and their salts may also form hydrates and solvates. In addition, the nitrogen atoms in groups R, (A), $R^3$ and $R^4$ may also form quaternary salts and N-oxides. Such derivatives are also deemed to be included in the compounds of the present invention.

It will also be appreciated by those skilled in the art that the compounds of this invention will have a tautomeric isomerism about the nitrogen and ring carbon atoms of the isothiazole ring; i.e., the exo-imino structure may exist at one or both of the N-atoms attached at the 3- and 4- positions of the isothiazole ring as shown below:

In addition, there exists the possibility of stereoisomerism in the instant compounds when p=1. These stereoisomers correspond to an R or S absolute configuration at the sulfur atom of the isothiazole ring. It is intended that all such stereoisomers are included within the instant invention.

As stated above, the compounds of this invention have been found to have pharmacological activity in the animal body as antagonists to certain actions of histamine which are not blocked by "antihistamines" such as mepyramine. For example, they have been found to inhibit selectively the histamine-stimulated secretion of gastric acid in the stomach of chronic fistula dogs at doses of from 0.01 to 10 mg per kilogram intravenously or orally from 0.01 to 50 mg per kilogram. Similarly, the action of these compounds is demonstrated by their antagonism to the effects of histamine on other tissues which are not affected by histamine H1 antagonists. An example of such tissue is the isolated guinea-pig right atrium.

These compounds have been found to be up to 100 times more active in animal models than cimetidine.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 15 mg to about 0.4 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to obtain the desired preparation.

The active ingredient will be present in the composition in an amount effective to inhibit histamine gastric acid secretory activity. The route of administration may be orally or parenterally.

Preferably, each daily dosage will contain the active ingredient in an amount of from about 5 mg to about 500 mg, most preferably from about 15 mg to about 150 mg given in a single dose or multiple divided doses.

For therapeutic use, the pharmacologically active compounds of the present invention will normally be administered as a pharmaceutical composition compris-

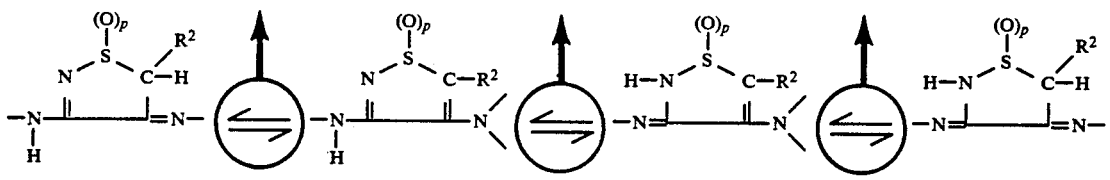

All of the various tautomeric structures of the instant compounds are intended to be included in this invention. In addition, when R is guanidino, three tautomers are possible as determined in the art, and all such tautomers are included in this invention.

ing at least one such compound as the sole or an essential active ingredient in the basic form or in the form of an addition salt with a pharmaceutically acceptable acid and in association with a pharmaceutical carrier therefor. Such addition salts include those mentioned above.

Other pharmacologically active compounds may, in certain cases, be included in the composition. It may be appropriate to combine the instant compound or compounds with anticholinergic agents such as propantheline; H1 antihistamines such as mepyramine, pyribenzamine chlorpheniramine and the like; or prostanoids.

Advantageously the composition will be made up in a dosage unit form appropriate to the desired mode of administration such as, for example, a tablet, capsule or injectable solution.

The compounds of this invention are synthesized by sequential reaction of the amines $$\begin{array}{c} R^3NR^1 \\ | \\ R^4 \end{array}$$

and $R(A)(CH_2)_nX(CH_2)_mNHR^1$ with either an isothiazole-1-oxide or 1,1-dioxide each substituted with an appropriate leaving group (Y, Z) in the 3- and 4-positions. (In intermediates II, Y and Z may be lower alkoxy, aryloxy, loweralkylthio, loweralkylsulfonyl, arylthio, arylsulfonyl, halo (F, Cl, Br, I), di-loweralkylamino and cyclicamino such as piperidino, morpholino, and the like.) It will be noted in the Reaction Schemes outlined below that position isomers Ia and Ib can be obtained from these reactions. The isomer Ia or Ib which results depends on several factors. These include the order of addition of the amine reagents mentioned above, the relative reactivity of the leaving groups (Y, Z) at positions -3 and -4, respectively, and the electronegativity of the substituent at the 5-position ($R^2$). The synthetic strategies outlined below demonstrate preparation of specific examples of Ia and Ib compounds by constructive utilization of the aforementioned considerations.

When $R^2$ is an electronegative substituent such as carboxy, carboalkoxy, cyano, carbamoyl, substituted carbamoyl, sulfamoyl, substituted sulfamoyl, alkanoyl, aroyl, and the like, compounds Ia and Ib are synthesized by addition of the amines III and IV to the isothiazoles of formula II as in Reaction Scheme I. When Y, Z are independently Cl, Br, loweralkoxy, or aryloxy and $R^2=CO_2R^9$ or $SO_2R^9$, the amine III or IV preferentially displaces Z. When $R^2=CN$, aryl or $CONR^3R^{7a}$, amines III or IV selectively displace Y. In the case where $R^2=CONH_2$ or $SO_2NH_2$, mixtures of intermediates V and VI can be obtained and separated by methods known in the art, such as column chromatography on silica gel or aluminum oxide. In Reaction Scheme I, $R^1$ is hydrogen or trimethylsilyl and R, $R^3$, $R^4$, (A), X, m and n are as previously defined.

The isothiazole intermediate II wherein p=2 is synthesized according to Reaction Schemes II–VI.

The isothiazole intermediate II (Reaction Scheme III) wherein p=1 and, for example, $R^2=CO_2R^9$, is synthesized by oxidation of the precursor XIV with one mole of alkyl, haloalkyl, or arylpercarboxylic acid ($R'=CH_3$, $CF_3$, m-chlorophenyl), dinitrogen tetroxide or chromic anhydride. Also, as outlined in Reaction Scheme IV, XXI is similarly converted to XXII and thence to XXIII.

In Reaction Scheme III, it can be seen that the leaving group Z can be introduced by electrophilic substitution of isothiazoles XVI by reaction with a suitable electrophile such as Y-Z (e.g. $Br_2$)

Some intermediates in Reaction Schemes I–III such as IIa, IIb, IIc, V, VI, IX, X, XI, XII, XIII and XIV are unknown in the art and are thus preferred intermediates and compounds of the instant invention. In particular, intermediates VIa and VIb (Reaction Scheme I) also possess the desired gastric antisecretory activity and are thus potentially useful in the treatment of gastric hypersecretory diseases such as peptic ulcers.

REACTION SCHEME I

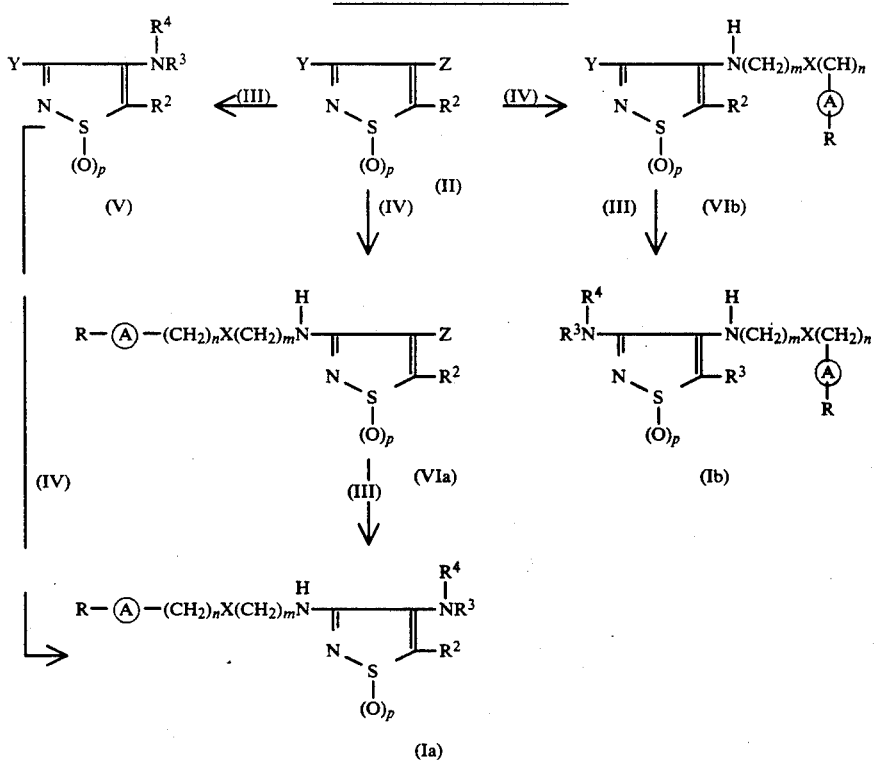

-continued
REACTION SCHEME I

III = R¹NR³R⁴
IV = R¹NH(CH₂)$_m$X(CH₂)$_n$-(A)-R

REACTION SCHEME II

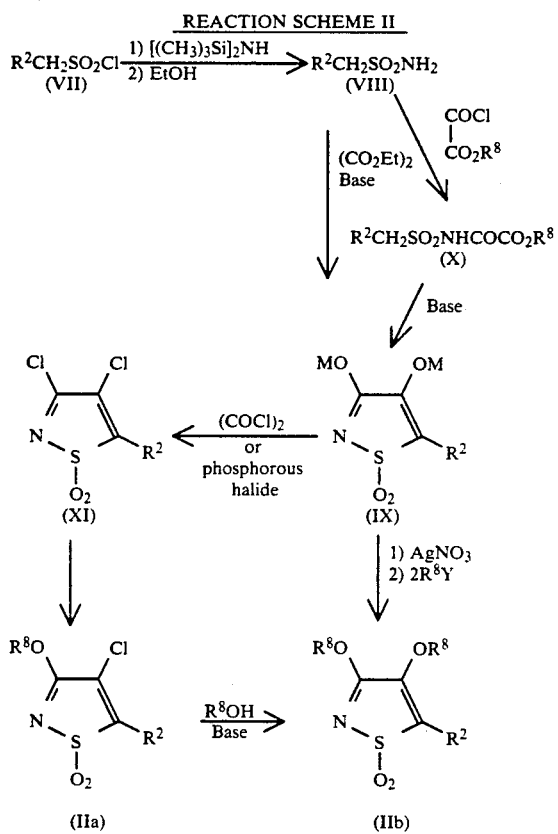

REACTION SCHEME III

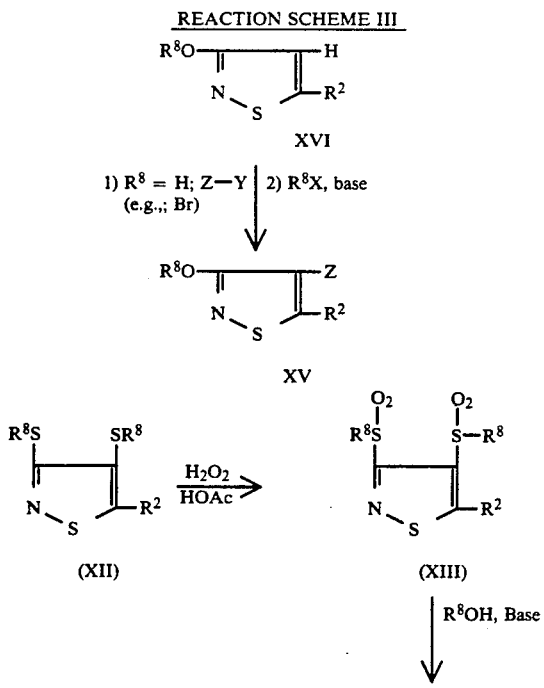

-continued
REACTION SCHEME III

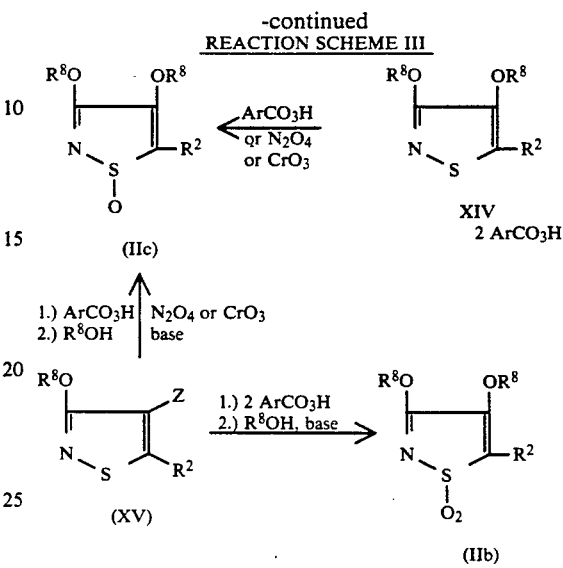

In Reaction Scheme I, wherein Y, Z of II are halogen and/or lower alkoxy, preferred compounds Ia are obtained by reacting II with the amines or N-trimethylsilyl amines III in inert solvents such as hydrocarbons or halocarbons, preferably methylene chloride, at temperatures of about −30° C. to +60° C., preferably 0°–25° C. and for one to 24 hours. If R' of III is trimethylsilyl, then the crude products V are treated with a lower alkanol, preferably ethanol, to remove trimethylsilyl groups. The compounds V are then reacted with complex amines or N-trimethylsilyl derivatives IV in hydrocarbon or halocarbon solvents, preferably methylene chloride, or in polar aprotic solvents such as acetonitrile, dimethyl sulfoxide, N,N-dimethylformamide, and the like, at temperatures of about 0° C. to the reflux temperature of the solvent for one to 24 hours to give preferred compounds Ia.

In Reaction Scheme II, intermediates IX can be formed by reaction of α-substituted methanesulfonamides VIII with oxalic esters, preferably diethyl oxalate, in lower alkanol solvents, preferably ethanol, at temperatures of about 25° C. to 100° C., preferably reflux temperature of the solvent, in the presence of from 2–2.5 equivalents of metal lower alkoxide, preferably sodium ethoxide, for 1 to 48 hours, or until precipitation of the desired dialkali metal salts IX is complete and thin layer chromatographic analysis shows no unreacted VIII. Alternatively, oxamate X can be formed by reaction of the α-substituted methanesulfonamides VIII with alkyl oxalyl chloride, preferably ethyloxalyl chloride, at 25° to 150° C., preferably 120° C., for 1–8 hours, preferably 2 hours. Intermediates X can be cyclized to IX in the presence of strong bases such as, for example, alkali metal alkoxides, preferably sodium tert-butoxide, in polar aprotic solvents, preferably N,N-dimethylformamide, at 0° to 60° C., preferably 25° C., for 1 to 24 hours. The intermediates IX can be reacted with phosphorus halides, such as phosphorus pentachloride and oxychloride, or reactive acyl halides, preferably oxalyl chloride, in hydrocarbon or halocarbon solvent or, in the absence of solvent, at 60° C.-150° C. for 1 to 48 hours. The desired dichloro intermediates XI are then reacted with loweralkanols, preferably ethanol (one equivalent), at −30° C. to 60° C. in halocarbon solvents for 30 minutes to 24 hours, preferably one hour, to give haloalkoxy intermediates IIa. The latter can be further reacted with alkanol, preferably ethanol, in the presence of bases, such as alkali carbonates and bicarbonates, pyridine, and loweralkylamines, preferably triethylamine, in aprotic solvents, preferably methylene chloride, at −30° C. to 50° C. preferably 0° C., to give diloweralkoxy intermediates IIb. The latter can also be synthesized by reacting intermediates IX with two equivalents of silver nitrate followed by two equivalents of alkylating agents $R^8$-Y in which Y is preferably $OSO_2OR^8$ bromine, iodine and $OSO_2$aryl and substituted aryl, in polar aprotic solvents such as acetonitrile, N,N-dialkylcarboxamides, diloweralkylsulfoxides, and the like, at temperatures of about 0° C. to 100° C., preferably 50°-80° C. By this method, a mixture of the desired IIb and its N-alkylated isomers are obtained and this mixture is separated by methods known to those skilled in the art.

Compounds XV required in Reaction Scheme III are obtained by electrophilic substitution of the 4-unsubstituted compounds XVI with reagent YZ, preferably bromine, in halocarbon or acetic acid solvent at a temperature of about 0° to 50° C.

In Reaction Scheme III, bis loweralkylthio intermediates XII are oxidized with hydrogen peroxide in acetic acid at temperatures of about 0° C. to 60° C. to give the bis-sulfones XIII. The latter can be reacted with lower alkanols in the presence of base, preferably sodium ethoxide in ethanol, at 0° C. to reflux to give intermediates XIV. The latter are oxidized to S-oxides IIc with oxidizing agents such as aromatic peroxycarboxylic acids, dinitrogen tetroxide, alkali metal persulfates, or chromic anhydride, in solvents such as halocarbons at 0° C. to 60° C. Alternatively, XIV may be oxidized to 1,1-dioxides IIb with two equivalents of aromatic peroxycarboxylic acids in halocarbon solvent at 0° C. to 60° C. The same intermediates (IIb, IIc) can be synthesized by similar oxidation of intermediates XV followed by reaction with lower alkanols in the presence of base under similar conditions to those employed in the conversion of XIII to XIV. In general, the route from XII is preferred when $R^2$ is an electron withdrawing substituent such as alkoxycarbonyl, carbamoyl, sulfamoyl, cyano, and the like. When $R^2$ is hydrogen, loweralkyl, and the like, the route from XVI is preferred.

REACTION SCHEME IV

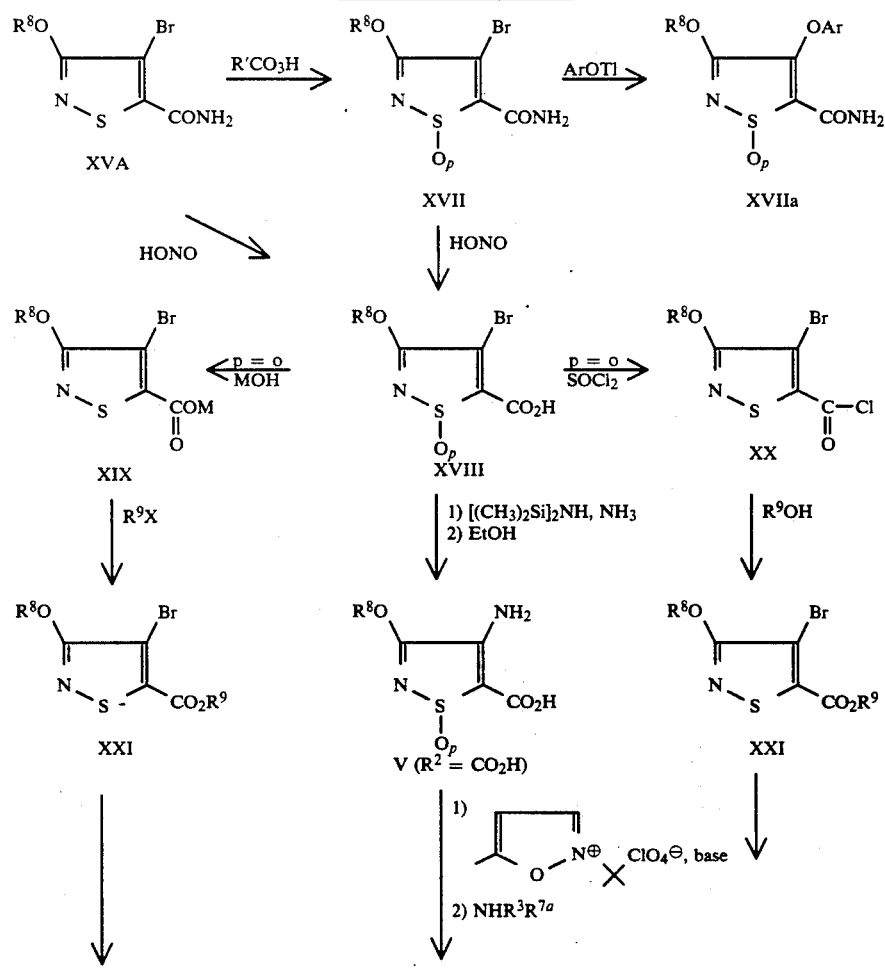

REACTION SCHEME IV

-continued

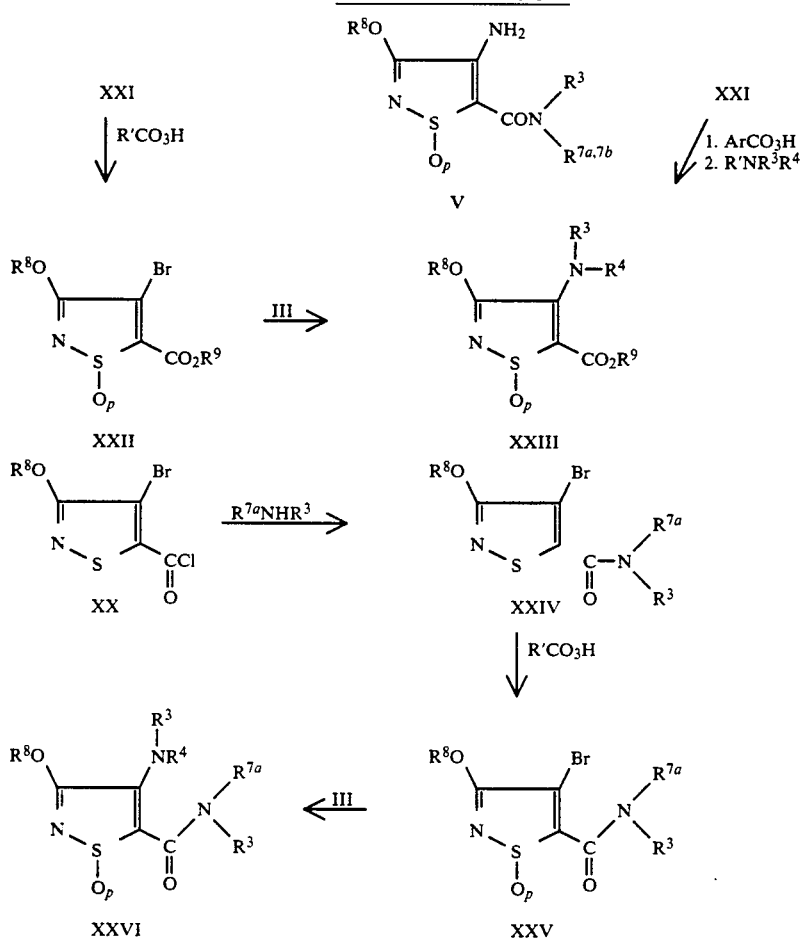

Reaction Scheme IV illustrates the conversion of 5-carbamoyl isothiazoles to useful synthons XVIII, XXII and XXV which are converted, respectively, to 5-carboxy, 5-alkoxycarbonyl and 5-substituted carbamoyl analogues of preferred compounds Ia and Ib. The key features of the transformations f Reaction Scheme IV are nitrous acid hydrolysis of the 5-carbamoyl function to a 5-carboxyl function and transformation of the 5-carboxyl function to esters and amides by methods known to those skilled in the art. Alternatively the carboxy synthon is converted to preferred compound Ia ($R^2 = CO_2H$) which is then converted to other Ia compounds in which

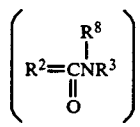

also by methods known in the art.

In certain cases for synthesis of preferred Ib compounds, intermediate XVII is preferentially first reacted with a metal (preferably thallium) phenoxide to displace Br and form XVIIa (Reaction Scheme IV) which is then sequentially reacted with N-trimethylsilylated amine IV ($R^1 = (CH_3)_3Si$) and ammonia to form Ib compounds (e.g. $R^2 = CONH_2$).

Reaction Scheme V

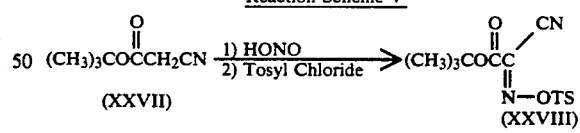

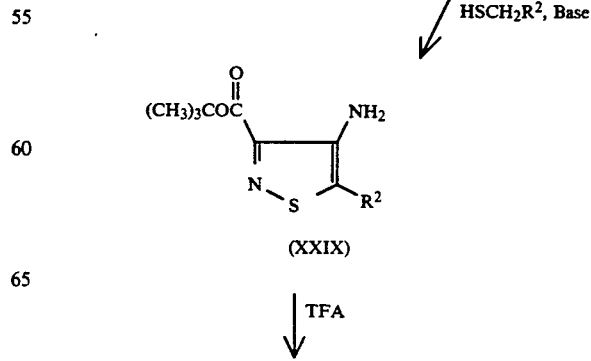

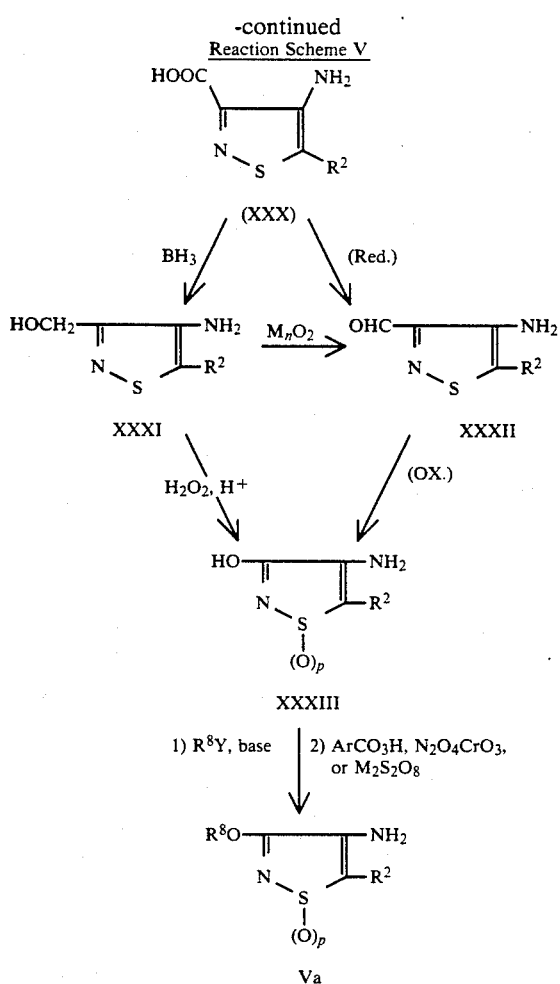

Compounds Ia, wherein $R^3=R^4=H$ and $p=1$ or 2, can also be made by addition of amines IV to intermediates Va, the latter being prepared according to Reaction Scheme V. Tert-butylcyanoacetate is converted to intermediates XXVIII, XXIX by procedures identified by K. Gewald and P. Bellmann (*Liebigs Ann. Chem.* 1979, 1534).

Selective solvolysis of the tert-butyl ester group of XXIX is achieved by dissolving it in trifluoroacetic acid, preferably at 10° to 40° C. The resulting carboxylic acid function of XXX can then be reduced to either the carboxaldehyde group of XXXII or the hydroxymethyl group of XXXI, either of which can be subjected to oxidative rearrangements resulting in intermediates XXXIII ($p=0$ or 1). For example, treatment of the hydroxy methyl compound XXXI with hydrogen peroxide under acidic conditions at 0° to 60° gives the rearranged intermediates XXXIII as a mixture wherein $p=0$ and $p=1$. The mixture is separated by methods known to those skilled in the art.

Alternatively, oxidative rearrangement of the carboxaldehyde XXXII under Baeyer-Villiger conditions, such as reaction with an equivalent of an aromatic peroxycarboxylic acid in a halocarbon solvent, preferably methylene chloride, at 0° to 65°, leads to intermediate XXXIII wherein $p=0$. These rearrangement products XXXIII can b alkylated with an equivalent of an alkylating agent $R^8$—Y, as described above for Reaction Scheme II, in polar aprotic solvents at 0° to 100° to form intermediates Va ($p=0$ or 1). The latter can be further oxidized at sulfur to $p=1$ or 2 with oxidizing agents such as aromatic peroxycarboxylic acids, dinitrogen tetroxide, chromic anhydride or alkali metal persulfates.

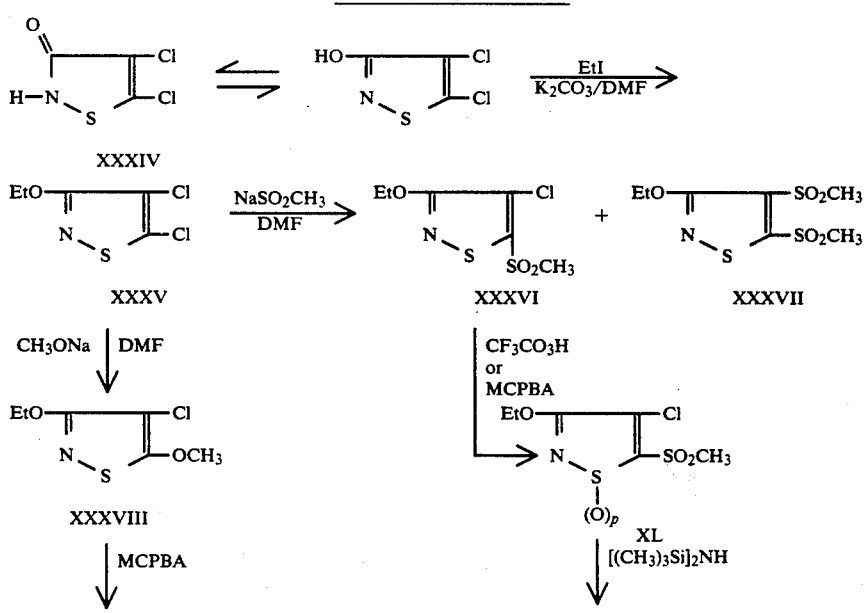

REACTION SCHEME VI -continued

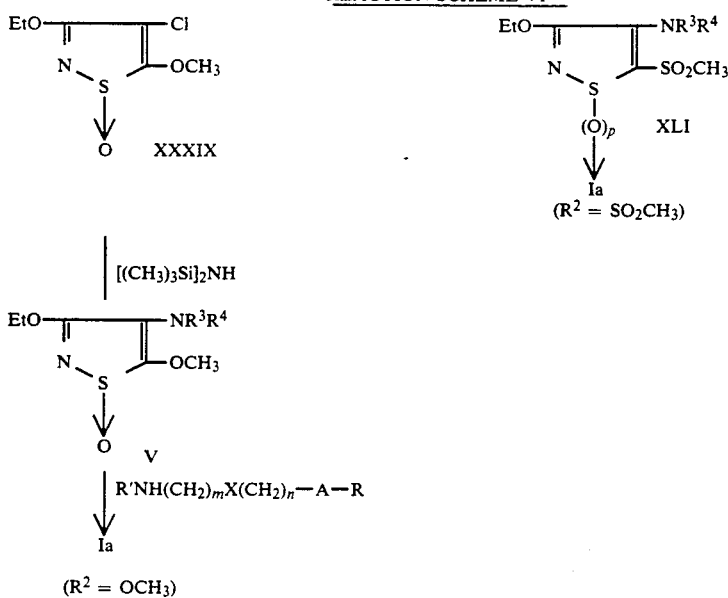

(R² = OCH₃)

Reaction Scheme VI illustrates the principle of displacement of a 5-halogen substituent of a suitably substituted isothiazole (e.g., XXXV) with nucleophiles such as loweralkoxide, loweralkylsulfenate, and loweralkylmercaptide in a polar aprotic solvent such as N,N-dimethylformamide at 0°-120° C., preferably 80°-120° C. The displacement products, XXXVI and XXXVIII, are converted to useful synthons, XXXIX and XLI, by the methods described hereinabove. These useful synthons are converted to preferred compounds Ia by methods described in Reaction Scheme I.

The following examples are provided to further illustrate the invention, but they are not to be construed as limitative of the invention. Unless otherwise indicated, all temperatures are in degrees Celsius.

EXAMPLE 1

Ethoxycarbonylmethane Sulfonamide

A solution of 54.6 g (0.29 mole) ethoxy carbonyl methanesulfonyl chloride in 250 ml methylene chloride was stirred at 0° under a nitrogen atmosphere while 46.8 g (0.29 mole) hexamethyldisilazane was added dropwise. The resulting cloudy solution was allowed to warm to 25° over one hour and then evaporated in vacuo to an oil which crystallizes: yield of the title product is 48.4 g (100%), mp 63°-67°; lit.¹ mp 67°-68°, lit² mp 66°-68°.

1.) *JACS* 1959, 81, 5655 R. L. Hinman, L. Locatelli, Jr.
2.) *Bull. Soc. Chim. Fr.* 1975 (3-4), 807 A. LeBerre, A. Etienne, B. Desmazieres

EXAMPLE 2

Disodium salt of 3,4-Dihydroxy-5-ethoxycarbonylisothiazole-1,1-dioxide

A solution of sodium ethoxide was prepared from 7.6 g (0.33 g-atom) sodium (spheres) in 200 ml abs. ethanol under a nitrogen atmosphere. At 25° a solution of 27.6 g (0.165 mole) ethoxycarbonyl methane sulfonamide in 200 ml ethanol was added to the ethoxide solution, following which was added dropwise a solution of 24.1 g (0.165 mole) diethyloxalate in 50 ml ethanol. The resulting thick suspension was warmed to reflux and stirred under reflux overnight. The mixture was cooled to 25°, filtered and the white solid washed with 100 ml abs. ethanol. The disodium salt, 41.4 g (95%1, can be recrystallized from 95% ethanol. The salt was stable as a hemihydrate (after drying at 95°/0.3 mm Hg over P₂O₅ for 24 hours); mp 265°-285° (dec).

Anal. Calcd. for $C_6H_5NO_6SNA_2.\frac{1}{2}H_2O$: C, 26.28; H, 2.21,; N, 5.11. Found: C, 26.08; H, 2.49; N, 5.12.

EXAMPLE 3

3-Ethoxy-4-chloro-5-ethoxycarbonylisothiazole-1,1-dioxide

In a dry flask fitted with a magnetic stirrer, condenser and calcium sulfate drying tube were placed 3.2 g , (0.011 mole) of the Example 2 disodium salt and 11.0 g (0.053 mole) phosphorous pentachloride. The flask was immersed in a preheated 100° oil bath and the mixture was stirred for 18 hours, following which phosphorous oxychloride was distilled off under aspirator pressure. The solid residue was slurried in 100 ml ether, the ether supernatant filtered rapidly into a clean, dry flask containing 15 ml absolute ethanol. The ether extraction of the residual solid was repeated three times with all ether-ethanol filtrates combine. After stirring at room temperature for 30 minutes, the ether-ethanol solution was concentrated in vacuo to an oily solid which was collected by suction filtration after trituration with a small amount of ether. This solid title compound weighed 890 mg (30%); mp 134°-136°, M/S: m/e 267 (M⁺), 222 (M—OC₂H₅), 135 (M—OC₂H₅—[-Cl—C≡C—C—O⁺]), 87 (Cl—C≡C—C—O⁺).

Anal. Calcd. for $C_8H_{10}ClNO_5S$: C, 35.90; H, 3.77; N, 5.23. Found: C, 35.70,; H, 3.84; N, 5.48.

Alternatively, five grams (18.9 mmol) of the dry disodium salt of Example 2 was treated with 5.0 ml of distilled oxalyl chloride under a nitrogen atmosphere. The resulting mixture was treated, with vigorous stirring, with a solution of 1 ml dry pyridine in 50 ml of toluene.

The vigorously stirred mixture was heated by a heat gun until gas evolution began. The reaction was then allowed to proceed exothermically until gas evolution ceased. Warming was then resumed and continued until there was no more gas evolution. The resultant dark mixture was concentrated in vacuo and the residue taken up in 100 ml of methylene chloride. The solution was then added to a magnetically stirred suspension of 70-230 MESH silica gel (25 g), previously stirred in absolute ethanol, the ethanol decanted off, and the silica gel then washed with 2×50 ml portions of methylene chloride by decantation) and the suspension stirred for one hour at room temperature. The silica gel mixture was filtered through glass fiber paper, the filtrate evaporated in vacuo and the residue taken up in chloroform. Filtration through a column of silica gel, eluting with chloroform, gave 2.4 g of 3-ethoxy-4-chloro-5-ethoxycarbonylisothiazole-1,1-dioxide as a white solid, mp 134°-136°.

EXAMPLE 4

3,4-Diethoxy-5-ethoxycarbonyl isothiazole-1,1-dioxide

Triethylamine (1.05 ml, 7.5 mmol) dissolved in 10 ml methylene chloride was added dropwise to a stirred solution of 2.0 g (7.5 mmol) of the Example 3 compound and 2.5 ml absolute ethanol in 10 ml methylene chloride at 0° C. When the addition was complete, the resulting solution was stirred an additional 30 minutes and then evaporated at 35° in vacuo to an oil. Chromatography over silica gel (elutant, methylene chloride) produced tlc homogeneous, title material, 1.6 g (80%), mp 129°-133°.

Anal. Calcd. for $C_{10}H_{15}NO_6S$: C, 43.31; H, 5.45; N, 5.05. Found: C, 43.21; H, 5.60; N, 5.30.

EXAMPLE 5

3-Ethoxy-4-amino-5-ethoxycarbonyl isothiazole-1,1-dioxide

Under a nitrogen atmosphere, a solution of 1.41 g (5.3 mmol) of the Example 3 compound in 15 ml of methylene chloride was stirred in an ice bath while a solution of 1.2 g (7.9 mmol) hexamethyldisilazane in 10 ml methylene chloride was added dropwise. The solution was allowed to warm to room temperature at which temperature stirring was continued for 18 hours. The solution was then evaporated in vacuo to an oil which was redissolved in 20 ml of a mixture of methylene chloride (15) -ethanol (5). After stirring at room temperature for one hour, the solution was again concentrated in vacuo, leaving a solid, 1.1 g (85%), m 163°-165°. Recrystallization from ethyl acetate provided analytically pure title compound, mp 172.5°-173°.

Anal. Calcd. for $C_8H_{12}N_2O_5S$: C, 38.71; H, 4.87; N, 11.28. Found: C, 38.76; H, 4.91; N, 11.40.

The title compound can also be prepared by an alternate route employing the Example 4 compound and hexamethyldisilazane following the above procedure.

From 690 mg (2.5 mmole) of the Example 4 compound and 600 mg (3.75 mmole) hexamethyldisilazane there was obtained 525 mg (85%) of the title compound, mp 168°-172°. Thin layer chromatography (silica GF, 95:5 CHCl₃:CH₃OH) showed this to be identical with the material prepared from the 3-ethoxy-4-chloro- compound; a mixed melting point was undepressed (169°-173°).

EXAMPLE 6

3,4-Diethoxy-5-cyanoisothiazole-1,1-dioxide

Step A Disodium 3,4-dihydroxy-5-cyanoisothiazole-1,1-dioxide

To a suspension of sodium hydride (1.8 g, 45 mmol) in dimethylformamide (10 ml) at 70° was added a solution of sulfamylacetonitrile (27 g, 22.5 mmol) in dimethylformamide (12 ml). Then a solution of diethyl oxalate (3.0 ml, 23 mmol) in dimethylformamide (10 ml) was added dropwise and the reaction temperature was raised to 100°. After 1 hour, the temperature was raised to 120° and maintained at that temperature for 15-20 hours. The reaction was then cooled, diluted with a small volume of ethanol, solids were filtered off, and the filtrate diluted with ethanol and diethyl ether to afford a gummy precipitate. This precipitate was dissolved in methanol, filtered and then diluted with diethyl ether to give the title compound as a tan solid (3.5 g) which was used without further purification.

Step B 3,4-Dihydroxy-5-cyanoisothiazole-1,1-dioxide disilver salt

To a solution of disodium 3,4-dihydroxy-5-cyanoisothiazole-1,1-dioxide (7.4 g, 34 mmol) in water (60 ml) there was added a solution of silver nitrate (11.5 g, 68 mmol) in water (40 ml). The resulting suspension was stirred for 2-3 hours and the precipitate collected by filtration and washed with ethanol, diethyl ether and dried to give 11.4 g of title compound which was used without further purification.

Step C 3,4-Diethoxy-5-cyanoisothiazole-1,1-dioxide

A solution of ethyl iodide (5.15 ml, 64 mmol) in acetonitrile (5 ml) was added dropwise to a suspension of diargento 3,4-dihydroxy-5-cyanoisothiazole-1,1-dioxide (11.4 g, 29 mmol) in acetonitrile (75 ml). This mixture was stirred for 2-3 days and then the silver salts were filtered and the filtrate evaporated. This residue was dissolved in chloroform and passed through a short column of silica gel to give 3.4 g of a 2:3 mixture of 3,4-diethoxy-5-cyanoisothiazole-1,1-dioxide and ethoxy-5-cyano-2-ethylisothiazole-3-one-1,1-dioxide.

This mixture (2.65 g, 11.5 mmol) was then dissolved in acetonitrile (10 ml) cooled in an ice-bath, and a solution of hexamethyldisilizane (1.37 ml, 0.0065 mmol) in acetonitrile (2 ml) was added dropwise. The solution was warmed to ambient temperature and then heated at 50° for 90 minutes. After cooling to ambient temperature, the solution was concentrated to dryness in vacuo. Methylene chloride (4 ml) was added and the charge was cooled in an ice-bath. Absolute ethanol (25 ml) was added, the mixture was warmed to ambient temperature and stirred for 30 min. The solution was concentrated to dryness in vacuo to give 2.44 g of a yellow solid which was chromatographed on a column of E. Merck silica gel 60. From the fractions eluted with chloroform followed by 2% acetonitrile/chloroform there was obtained 0.97 g 3,4-diethoxy-5-cyanoisothiazole-1,1-dioxide. This 90% pure product was (90% pure by NMR) recrystallized from 2:1 n-butylchloride:hexane to give 0.84 g (78% of theoretical) pure title compound, mp 147°-148.5°.

TLC (10% methanol/chloroform, silica): Rf=0.7
Calc'd for $C_8H_{10}N_2O_4S$: N, 12.17; C, 41.73; H, 4.38. Found: N, 12.29; C, 41.88; H, 4.50.

EXAMPLE 7

3-Ethoxy-4-amino-5-ethoxycarbonylisothiazole-1-oxide

Step A 3-Ethoxy-4-bromo-5-chlorocarbonylisothiazole

3-Ethoxy-4-bromo-5-carboxyisothiazole (2.52 g, 0.01 mol) was heated at reflux in 25 ml of thionyl chloride for ¼ hour. Removal of the excess thionyl chloride in vacuo gave 2.7 g of the title compound as an off white solid, mp 58.5°–61° C.

Step B 3-Ethoxy-4-bromo-5-ethoxycarbonylisothiazole

3-Ethoxy-4-bromo-5-chlorocarbonylisothiazole (2.7 g, 0.01 mol) in 25 ml of absolute ethanol was heated at reflux for ½ hour. Removal of the ethanol in vacuo gave 2.8 g of off white solid, mp 40°–43° C.

Step C
3-Ethoxy-4-bromo-5-ethoxycarbonylisothiazole-1-oxide and 1,1-dioxide

3-Ethoxy-4-bromo-5-ethoxycarbonylisothiazole (95 mg, 0.34 mmol) was dissolved in 2 ml of methylene chloride and m-chloroperbenzoic acid (58.7 mg, 0.34 mmol) was added in small portions over ten minutes. The reaction mixture was stirred at rom temperature over night. The reaction mixture was then concentrated in vacuo and the residue was chromatographed on silica gel using chloroform. There was obtained 22 mg of the 1,1-dioxide melting at 145°–146° and 17 mg of the 1-oxide melting at 93°–94° C.

Step D
3-Ethoxy-4-amino-5-ethoxycarbonylisothiazole-1-oxide

3-Ethoxy-4-bromo-5-ethoxycarbonylisothiazole-1-oxide (1.48 g, 5.0 mmol) was dissolved in fifteen ml of dry acetonitrile. The solution was cooled in ice and a solution of anhydrous ammonia in cold acetonitrile (0.105 mol in 5 ml) was added dropwise in excess. After stirring in the ice bath for 4¼ hours the reaction was complete. The title compound (1.16 g 78%, mp 153.5°–155° C.) was obtained as a yellow solid by chromatography on silica gel (chloroform).

EXAMPLE 8

3-Amino-4-ethoxy-5-cyanoisothiazole-1,1dioxide

To a suspension of 3,4-diethoxy-5-cyanoisothiazole-1,1-dioxide (0.85 g, 0.0037 mol) in 40 ml of ethanol was added 2.6 ml of 1.7M ammonia in ethanol (0.0044 mol) with stirring. A clear yellow solution formed and a white precipitate separated in 5 minutes. After 2 hours at room temperature, the title compound (0.61 g, 82%, mp 232°–233.5°) was collected and a sample recrystallized from ethanol to give analytically pure material, mp 236°–238.5°, Rf 0.26 (10% methanol-chloroform, silica gel).

Calcd for $C_6H_7N_3O_3S$: N, 20.89; C, 35.81; H, 3.51. Found: N, 21.02, C, 35.91; H, 3.59.

EXAMPLE 9

3-Ethoxy-4-amino-5-cyanoisothiazole-1,1-dioxide ( Step A
3-Ethoy-4-chloro-5-cyanoisothiazole-1,1-dioxide 3,4-Dihydroxy-5-cyanoisothiazole-1,1-dioxide disodium salt from Example 6, Step A (23.6 g, 0.10 mol) was reacted with oxalyl chloride (45 ml) according to the alternate procedure of Example 3 to give crude 3-ethoxy-4-chloro-5-cyanoisothiazole-1,1-dioxide.

Step B
3-Ethoxy-4-amino-5-cyanoisothiazole-1,1-dioxide

The product from Step A was reacted with hexamethyldisilazane followed by ethanol according to the procedure of Example 5. After recrystallization of the crude product from ethanol, there was obtained pure title compound, mp 228°–229°.

EXAMPLE 10

3-Amino-4-ethoxy-5-N,N-dimethylcarbamoylisothiazole-1,1-dioxide

Step A Disodium
3,4-Dihydroxy-5-dimethylcarbamylisothiazole-1,1-dioxide

To a suspension of 60% NaH (5.0 g, 0.125 mol) in dry DMF (10 ml) under a nitrogen atmosphere at 70° C. was added dropwise a warmed solution of N,N-dimethyl-α-sulfanylacetamide (10.1 g, 0.061 mol) in DMF (55 ml). After ½ hour, a solution of diethyl oxalate (8.7 ml, 0.064 mol) in DMF (20 ml) was added dropwise and the solution was allowed to heat at 120° C. for 12–16 hours. After cooling the reaction, it was diluted with ethanol and the precipitated product collected by filtration, washed with ethanol, ether and dried in vacuum oven at 70° C. for several hours to give 16.5 g of crude title compound.

Step B
3,4-Dihydroxy-5-dimethylcarbamylisothiazole-1,1-dioxide Disilver salt

The crude disodium salt from part A was dissolved in water (150 ml) and added dropwise to a solution of silver nitrate (23.0 g, 0.135 mol) in water (150 ml). An immediate gelatinous precipitate formed, but after stirring for 3–5 hours, a more granular brownish precipitate was obtained. This was filtered, washed with water, ethanol, ether and dried in a vacuum oven at 70° C. for several hours to give 1.6 g of crude title compound.

Step C
3,4-Diethoxy-5-dimethylcarbamylisothiazole-1,1-dioxide

To a suspension of 3,4-dihydroxy-5-dimethylcarbamylisothiazole-1,1-dioxide disilver salt (8.0 g, 17.9 mmol) in acetonitrile (30 ml) was added ethyl iodide (4.3 ml, 54 mmol). This mixture was stirred at ambient temperature for 2–3 days. The precipitated silver salts were removed by filtration and the acetonitrile solution evaporated to give 5.4 g of residue containing the title compound at a ratio of 2:3 to its isomeric 2-ethyl-4-ethoxy-5-dimethylcarbamyl-3-isothiazolone. This residue was chromatographed on silica gel eluting with chloroform to give 1.3 g of purified isomeric mixture enriched in the title compound (60%). No further attempt as made to purify this material.

Step D
3-Amino-4-ethoxy-5-dimethylcarbamylisothiazole-1,1-dioxide

To a solution of 60% pure 3,4-diethoxy-5-dimethylcarbamylisothiazole-1,1-dioxide (1.3 g) from Part C in acetonitrile (7 ml), under nitrogen, was added hexamethyldisilizane (0.90%, 4.3 mmol). This solution was heated at 50° for four hours. The reaction was then quenched with methanol (0.5 ml) and the solvent evaporated. This residue was chromatographed on silica gel eluting with 40% methanol/chloroform and the collected product residue triturated with ether to give 0.61 g, of title compound (mp 221°–223°).

EXAMPLE 11

3-Ethoxy-4-chloro-5-methanesulfonylisothiazole

Step A 3-Ethoxy-4,5-dichloroisothiazole

To a mixture of 4,5-dichloro-3-hydroxyisothiazole (17.00 g, 0.100 mol) and potassium carbonate (13.82 g, 0.100 mol) in dry DMF (80 ml) was added dropwise a solution of ethyl iodide (8.84 ml, 0.110 mol) in dry DMF (20 ml). The mixture was stirred 18 hours at ambient temperature. Water (500 ml) was added and the mixture was extracted with ether (3×400 ml). The combined ether extracts were dried over sodium sulfate, filtered, and concentrated in vacuo to give the crude product (18.35 g). The crude product was distilled to give 4,5-dichloro-3-ethoxyisothiazole (14.63 g, 74%, b.p. 64°–66°/0.1 mm). TLC (2% methanol/chloroform, silica): Rf=0.72.

Step B 3-Ethoxy-4-chloro-5-methylsulfonylisothiazole

To a solution of 3-ethoxy-4,5-dichloroisothiazole (19.8 g, 0.10 mol) in DMF (50 ml) under a nitrogen atmosphere was added sodium methanesulfenate (20.4 g, 0.20 mol). The mixture was warmed to 100° C. and stirred for two days. The reaction mixture was then cooled, diluted with diethyl ether, washed with water, dried over anhydrous sodium sulfate, filtered, and concentrated in vacuo. The residue was chromatographed on a silica gel column, eluting with chloroform, to give 7.1 g of the title compound, mp 85°–87°, crystallized from cyclohexane. A by-product, 3-ethoxy-4,5-bis(methylsulfonyl)isothiazole (3.9 g) was also obtained, mp 158°–160° (crystallized from cyclohexane).

EXAMPLE 12

3-Ethoxy-4-chloro-5-methoxyisothiazole-1-oxide

Step A 3-Ethoxy-4-chloro-5-methoxyisothiazole

To a solution of 3-ethoxy-4,5-dichloroisothiazole (1.0 g, 5.1 mmol) in DMF (5 ml) under a nitrogen atmosphere was added sodium methoxide (570 mg, 10.5 mmol). The mixture was warmed to 100° C. and stirred for eight hours. The reaction mixture was then cooled, diluted with diethyl ether, washed with water, dried over anhydrous sodium sulfate, filtered, and concentrated in vacuo. The residue was chromatographed on a silica gel column, eluting with cyclohexane and then toluene, to give 170 mg of the title compound.

Step B
3-Ethoxy-4-chloro-5-methoxyisothiazole-1-oxide

A solution of m-chloroperoxybenzoic acid (100 mg, 0.49 mmol) in methylene chloride (1.5 ml) wad added dropwise with stirring to an ice-cooled solution of 3-ethoxy-4-chloro-5-methoxyisothiazole (87 mg, 0.45 mmol) in methylene chloride (1.0 ml). The solution was then stirred for 12 hours at room temperature. The m-chlorobenzoic acid, which precipitated out of solution, was filtered off. The filtrate was concentrated in vacuo, and the residue was chromatographed on a silica gel column, eluting with toluene followed by chloroform, to give 40 mg of the title compound.

Alternate synthesis of:
3-Ethoxy-4-chloro-5-methoxyisothiazole-1-oxide

To the solution of 3-ethoxy-4,5-dichloroisothiazole-1-oxide (0.12 g, 0.00056 mol) in methanol (1 ml) cooled in an ice-bath was added a solution of sodium methoxide (0.032 g, 0.00060 mol) methanol (1 ml). The solution was warmed to ambient temperature and stirred overnight. The solution was concentrated to dryness in vacuo and the residue was partitioned between chloroform (10 ml) and water (5 ml). The aqueous layer was washed with chloroform (10 ml) and the combined organic layers were washed with saturated sodium chlorate solution (2 ml) dried over sodium sulfate, filtered, and concentrated to dryness to give 0.14 g orange liquid. This liquid was chromatographed on a column of E. Merck silica gel 60. From the fraction eluted with n-butylchloride, there was obtained 0.06 g of a mixture of starting material and 3-methoxy-4,5-dichloroisothiazole-1-oxide. From the fractions eluted with methylene chloride, there was obtained 0.03 g (25%) of the title compound. TLC (methylene chloride silica): Rf=0.43 (identical to product of Step B above.

EXAMPLE 13

Step A
3-Ethoxy-4-chloro-5-methylsulfonylisothiazole-1-oxide

To a solution of 3-ethoxy-4-chloro-5-methylsulfonylisothiazole (1.9 g, 8 mmol) in methylene chloride (10 ml), cooled in an ice bath was added dropwise a solution of pertrifluoroacetic acid (9 mmol) in methylene chloride (10 ml). After stirring for 2 hours, the reaction was diluted with methylene chloride and washed with sodium bisulfite solution, sodium bicarbonate solution, dried over anhydrous sodium sulfate, filtered and evaporated. The residue obtained from diethyl ether gave 1.5 g of a 1:1 mixture of the title compound and starting material. This material was used in subsequent reactions. Repeated recrystallizations from diethyl ether gave pure product, mp 98°–102°.

Step B
3-Ethoxy-4-amino-5-methylsulfonylisothiazole-1-oxide

To a solution of crude 3-ethoxy-4-chloro-5-methylsulfonylisothiazole-1-oxide (0.90 g, 1.6 mmol) in acetonitrile (10 ml) under a nitrogen atmosphere was added hexamethyldisilizane (0.70 ml, 3.3 mmol). The reaction mixture was heated at 70° for 1½ hours, cooled to room temperature and methanol (1.0 ml) was added. The reaction was filtered and evaporated. The residue was triturated with methanol/ethyl acetate to afford crude title compound (0.3 g). Recrystallization from methanol/ethyl acetate after treatment with charcoal gave 0.23 g of pure product, mp 191°–193°.

EXAMPLE 14

3-Ethoxy-4-amino-5-methylsulfonylisothiazole-1,1-dioxide

Step A
3-Ethoxy-4-chloro-5-methylsulfonylisothiazole-1,1-dioxide

To a solution of 3-ethoxy-4-chloro-5-methylsulfonylisothiazole (2.0 g, 8.3 mmol) in chloroform (40 ml) was added 80% pure m-chloroperbenzoic acid (3.9 g, 18.2 mmol). This solution was stirred for 2–3 days as the m-chlorobenzoic acid by-product precipitated. The entire mixture was evaporated and the residue treated with diethyl ether. The crystalline title compound remained undissolved and was collected by filtration (1.5 g), mp 181°–184°.

Step B
3-Ethoxy-4-amino-5-methylsulfonylisothiazole-1,1-dioxide

To a solution of 3-ethoxy-4-chloro-5-methylsulfonylisothiazole-1,1-dioxide (1.1 g, 4.0 mmol) in acetonitrile (15 ml) under a nitrogen atmosphere was added hexamethyldisilizane (0.85 ml, 4.0 mmol). After an immediate exothermic reaction, the solution was heated at gentle reflux for 1 hour. Upon cooling to room temperature, methanol (1.0 ml) was added and any solid removed by filtration. The organic solution was evaporated and the solid residue triturated with ethyl acetate/methanol to give crystalline title compound (0.81 g), mp 214°–217°.

EXAMPLE 15
3-Ethoxy-4,5-dichloroisothiazole-1-oxide

To a solution of 3-ethoxy-4,5-dichloroisothiazole (13.86 g, 0.070 mol) in chloroform (100 ml) cooled in an ice-bath was added dropwise over 2 hours 85% m-chloroperbenzoic acid (14.21 g, 0.070 mol) in chloroform (200 ml). The mixture was warmed to ambient temperature and stirred for 18 hours. The mixture was cooled to 5° and filtered to remove 8.1 g m-chlorobenzoic acid. The filtrate was concentrated to dryness in vacuo, the residue triturated with 30 ml chloroform, and filtered to remove 3.8 g acid. The filtrate was concentrated and the residue was chromatographed on a column of E. Merck silica gel 60. From the fraction eluted with n-butylchloride, there was recovered 4.62 g (33%) starting material. From the fractions eluted with 1:1 n-butylchloride: methylene chloride there was obtained 4.56 g of a mixture of starting material, product, and 3-ethoxy-4,5-dichloro-isothiazole-1,1-dioxide. From the fraction eluted with 1:1 n-butyl-chloride: methylene chloride followed by methylene chloride there was obtained 7.48 g (50%) product, mp ca: 20°. TLC ($CH_2Cl_2$, silica): $Rf=0.53$.

EXAMPLE 16
3-Ethoxy-4,5-dichloroisothiazole-1,1-dioxide

To a mixture of 3-ethoxy-4,5-dichloroisothiazole, isothiazole-1-oxide, and isothiazole-1,1dioxide (5.26 g) obtained as in Example 15 dissolved in chloroform (50 ml) was added dropwise during 20 minutes a solution of 85% n-chloroperbenzoic acid (5.08 g, 0.0250 mol) in chloroform (70 ml) at ambient temperature. The resulting solution was stirred 2–5 days then concentrated to dryness in vacuo. The residue was triturated with chloroform (15 ml) and filtered to remove 2.5 g m-chlorobenzoic acid. The filtrate was concentrated to dryness to give 7.6 g residue which was chromatographed on a column of E. Merck silica gel 60. From the fractions eluted with n-butylchloride there was obtained 2.89 g of the title product, mp 120°–122.5°. TLC (methylene chloride, silica): $Rf=0.73$. A sample was recrystallized from n-butylchloride, mp 122.5–123.5.

Calc'd for $C_5H_5Cl_2NO_3S$: N, 6.09; C, 26.10; H, 2.19. Found: N, 5.97; C, 26.44; H, 2.18.

EXAMPLE 17
3-Hydroxy-4-bromo-5-carbamoylisothiazole

3-Hydroxy-5-carbamoylisothiazole (1.44, 0.01 mmol) was dissolved in 15 mol of trifluoroacetic acid. Bromine (2.4 g, 0.015 mmol) in 5 ml of trifluoroacetic acid was added dropwise over a 20 minute period. Simultaneously, at the same rate, water was added dropwise until 20 ml was added. Yellow solid separated when most of the water was added. The resulting suspension was stirred for two hours at room temperature, poured into 100 ml of ice water, and filtered to give the title compound as a white solid (1.5 g, 67%, mp 250°–251° C., dec).

EXAMPLE 18
3-Ethoxy-4-bromo-5-carbamoylisothiazole

3-Hydroxy-4-bromo-5-carbamoylisothiazole (0.6 g, 2.7 mmol) was dissolved in 5 ml of dry dimethylformamide. Potassium carbonate (0.37 g, 2.7 mmol) and ethyl iodide (0.46 g, 2.9 mmol) were added and the mixture stirred at room temperature for sixteen hours overnight. The dimethylformamide was removed in vacuo and the solid residue stirred in 0–15 ml of ice water. Filtration gave 0.5 g of white solid; mp 157°–162° C. (from methylene chloride); yield, 74%.

EXAMPLE 19
3-Ethoxy-4-bromo-5-carboxyisothiazole

3-Ethoxy-4-bromo-5-carbamoylisothiazole (2.51 g, 0.01 mol) was dissolved in 20 ml of trifluoroacetic acid and the solution cooled to 0° to 5° C. Sodium nitrite (2.76 o, 0.04 mol) was added in small portions to the stirred solution over a five minute period. Stirring was continued for 10 minutes at the same temperature and the reaction mixture poured into 150 ml of ice water. The title compound separated as a white solid (2.2 g, 88%, mp 151°–152.5° C.) and was filtered, washed with ice water and dried.

EXAMPLE 20
3-Ethoxy-4-bromo-5-chlorocarbonylisothiazole

A suspension of 3-ethoxy-4-bromo-5-carboxyisothiazole (5.0 g, 0.0198 mol) in 35 ml of thionyl chloride was stirred at reflux for 1 hour. The resulting yellow solution was concentrated in vacuo to obtain 5.3 g of the acid chloride as a pale yellow solid, m.p. 60°–62° C.

EXAMPLE 21
3-Ethoxy-4-bromo-5-t-butyloxcarbonylisothiazole

To a solution of dry t-butyl alcohol (1.63 g, 0.022 mol) in 5 ml of tetrahydrofuran was added dropwise 14.3 ml (0.021 mol) of n-butyl lithium reagent (1.47M in hexane) at ice bath temperature stirred for an additional ½ hour at room temperature and then added dropwise a solution of 3-ethoxy-4-bromo-5-chlorocarbonylisothiazole (5.4 g, 0.0198 mol) in 10 ml of THF. The mixture was heated at reflux for ½ hour after which it was concentrated in vacuo. The residual oil-solid mixture was taken up in 50 ml of ether and was washed with a little ice-water and with cold saturated $NaHCO_3$ solution. The ether extract was dried over anhydrous $Na_2SO_4$, filtered and concentrated in vacuo to obtain 5.9 g of the t-butyl ester as a yellow solid. Recrystallized m.p. was 46°–47.5° C. (pet. ether)

Calc'd for $C_{10}H_4BrNO_3S$: N, 4.55; C, 38.97; H, 4.58.
Found: N, 4.62; C, 39.28; H, 4.90.

EXAMPLE 22

3-Ethoxy-4-bromo-5-t-butyloxycarbonylisothiazole-1,1-dioxide

A solution of peroxytrifluoroacetic acid was prepared by standard procedures from 90% $H_2O_2$ (1.4 ml, 0.05 mol) and trifluoroacetic anhydride (12.6 g, 0.06 mol) in 25 ml of methylene chloride.

To a stirred solution of 3-ethoxy-4-bromo-5-t-butyloxycarbonylisothiazole (3.08 g, 0.01 mol) in 25 ml of methylene chloride was added anhydrous $Na_2CO_3$ (21.2 g, 0.2 mol) followed by the dropwise addition at 0° C. of the peroxytrifluoroacetic acid solution prepared above. The reaction mixture was filtered and the filtrate was cooled and washed quickly with cold sodium bicarbonate solution and with ice water. The methylene chloride solution was dried over anhydrous $Na_2SO_4$, filtered and concentrated in vacuo to obtain 3.0 g of the sulfone as a yellow solid. The product recrystallized from n-butyl chloride-hexane, m.p. 143°-145° C. with dec.

Calc'd for $C_{10}H_{14}BrNO_5S$: N, 4.12; C, 35.30; H, 4.15.
Found: N, 4.00; C, 35.67; H, 4.19.

EXAMPLE 23

3-Ethoxy-4-amino-5-t-butyloxycarbonylisothiazole-1,1-dioxide

To 3-ethoxy-4-bromo-5-t-butyloxycarbonylisothiazole-1,1-dioxide (340 mg, 1.0 mmol) in 5 ml of dry acetonitrile was added hexamethyldisilazane (242 mg, 1.5 mmol) and the solution was stirred at reflux for 7 hours. The reaction mixture was evaporated in vacuo and the residue was refluxed in 10 ml of ethanol for ¾ hr. Removal of the ethanol in vacuo gave a crude oil which was chromatographed on silica gel. The product was recovered as a viscous yellow oil (210 mg). Trituration in petroleum ether gave a yellow solid, m.p. 128°-130° C. Mass spectral analysis confirmed the structure.

EXAMPLE 24

3-Ethoxy-4-bromo-5-carbamoylisothiazole-1-oxide and 1,1-dioxide

Pertrifluoroacetic acid was prepared from 0.36 ml of 90% hydrogen peroxide and 1.44 ml of trifluoroacetic anhydride in 10 ml of dry methylene chloride. This solution was added dropwise over a ¾ hour period to 3-ethoxy-4-bromo-5-carbamoylisothiazole (1.8 g, 7.0 mmol) in 50 ml of dry methylene chloride. After the solution was stirred at room temperature overnight, it was concentrated in vacuo to a volume of 5 ml. Chromatography of this concentrate on silica gel gave the title compounds. The 1-oxide (0.94 g) melts at 179°-181.5° C. while the 1,1-dioxide (0.6 g) melts at 168°-172° C.

EXAMPLE 25

3-Ethoxy-4-bromo-5-carboxyisothiazole-1-oxide

3-Ethoxy-4-bromo-5-carbamoylisothiazole-1-oxide (267 mg, 1.0 mmol) was dissolved in 2 ml of trifluoroacetic acid and sodium nitrite (138 mg, 2.0 mmol) was added in small portions over a two minute period with stirring. Stirring was continued for two minutes at room temperature and then the solvent was removed in vacuo. The residual gum was stirred in 5 ml of ice water for five minutes. Filtration gave 174 mg (65% yield) of yellow solid; mp 158°-160° C., dec.

EXAMPLE 26

3-Ethoxy-4-bromo-5-[N(2-dimethylamino)ethyl]carbamoylisothiazole-1-oxide

The product from Example 25, (4.4 g, 0.02 mol) can be added to a solution of dicyclohexylcarbodiimide (4.1 g, 0.02 mol) in 100 ml of dry acetonitrile. After about one hour, a solution of N,N-dimethylethylenediamine (1.8 g, 0.02 mol) in 25 ml of acetonitrile can be added dropwise at 0° C. The mixture can then be stirred at 0° for about four hours, filtered, and concentrated under vacuum at 25° C. The residue can be triturated with ice water and the solid title compound can be collected by suction.

EXAMPLE 27

3-Ethoxy-4-amino-5-[N[(2-hydroxy)ethyl[carbamoyl]-isothiazole-1-oxide

The product from Example 25, (5.8 g, 0.02 mole) can be added to a solution of triethylamine (28 ml, 0.02 mol) and diphenylphosphorylazide (5.5 g, 0.02 mol) in 100 ml of dry acetonitrile at 0° C. A solution of ethanolamine (1.23 g, 0.02 mol) in 25 ml of acetonitrile can then be added dropwise with stirring under $N_2$ at 0°. The mixture can then be stirred for about four hours at 0° C., diluted with one volume of ice water and the precipitated title compound can be collected by suction.

EXAMPLE 28

3-Methoxy-4-amino-5-methylisothiazole-1,1-dioxide

Step A

3-Hydroxy-4-amino-5-methylisothiazole-1,1-dioxide Potassium Salt

4-Chloro-5-methylisothiazole-3-one-1,1-dioxide (S. N. Lewis et al., J. Heterocyclic Chem. 8, 1971, 591) (9.0 g, 0.05 mol) can be added to a solution of ammonia in absolute ethanol (200 ml of 0.06 molar). The suspension can then be stirred for about four hours at room temperature and then added to a solution of potassium hydroxide (5.6 g, 0.10 mol) in 200 ml of ethanol. The resulting suspension should then be stirred for about one hour at room temperature and filtered. The resulting solid can then be recrystallized from water to give the potassium salt of 4-amino-5-methylisothiazoline-3-one-1,1-dioxide which can be subsequently dried at about 80° under high vacuum.

Step B

3-Methoxy-4-amino-5-methylisothiazole-1,1-dioxide

The product from Step A, (60 g, 0.03 mol) can be dissolved in 50 ml of dimethylsulfoxide under $N_2$ at 50° C. and the stirred solution can be treated with dimethylsulfate (3.78 g, 0.03 mol) at about 50°. The stirred mixture can be kept at about 50° C. for about 3 hours, concentrated under vacuum and the residual semi-solid triturated with ice water and filtered to give the title compound.

EXAMPLE 29

3-Methoxy-4-bromoisothiazole-1-oxide

To a solution of 3-methoxy-4-bromoisothiazole (2.9 g, 15 mmol) in methylene chloride (15 ml) there can be was added, in portions, 3,5-dinitroperbenzoic acid (3.4 g, 15 mmol) with ice bath cooling. After about one hour, the precipitated 3,5-dinitrobenzoic acid can be filtered off and the solvent evaporated in vacuo. By triturating the residue with diethyl ether, a crystalline product, 3-methoxy-4-bromoisothiazole-1-oxide, can be obtained. Additional material can be obtained by chromatographing the mother liquors on silica gel, eluting with chloroform.

EXAMPLE 30

3-Methoxy-4-bromoisothiazole-1,1-dioxide

To a solution of 3-methoxy-4-bromoisothiazole (2.9 g, 15 mmol) in methylene chloride (10 ml) there can be added dropwise with ice-bath cooling a solution of 85% pure 3-chloroperbenzoic acid (6.09 g, 30 mmol) in methylene chloride (25 ml). When the addition is complete, the reaction mixture can be concentrated to one-half volume on a rotary evaporator, the mixture cooled in an ice bath, and 3-chlorobenzoic acid can be filtered off. The solvent can be evaporated in vacuo and the residue triturated with diethyl ether to afford the title compound. Additional product can be obtained by chromatography on silica gel, eluting with chloroform.

EXAMPLE 31

3,4-Dimethoxyisothiazole-1-oxide

To a solution of the Example 29 compound (1.05 g, 5 mmol) in methylene chloride (10 ml) there can be added with ice bath cooling, excess methanol (2.0 ml), followed by triethylamine (0.5 ml, 5 mmol). Upon stirring at ambient temperature for about 5 hours, the reaction mixture can be diluted with diethylether and the triethylamine hydrobromide removed by suction filtration. The filtrate can then be evaporated in vacuo to afford the title compound.

EXAMPLE 32

3,4-Dimethoxyisothiazole-1,1-dioxide

The title compound can be obtained following the procedures described in Example 31 except that the compound of Example 30 should be used in place of the compound of Example 29.

EXAMPLE 33

3-Amino-4-methoxyisothiazole-1-oxide

A solution containing 800 mg (5.0 mmol) of the Example 31 compound and 800 mg (5.0 mmol) hexamethyldisilazane in 10 ml dry acetonitrile can be stirred under nitrogen in an oil bath at about 50° C. After about 18 hours the solution can be evaporated to dryness in vacuo and the residue dissolved in 10 ml methanol. After stirring for about one hour, the mixture can then be concentrated in vacuo and the residue triturated with diethyl ether to afford the title compound.

EXAMPLE 34

3-Amino-4-methoxyisothiazole-1,1-dioxide

To a solution of the Example 32 compound (1.15 g, 6.5 mmol) in 15 ml of methylene chloride there can be added, under a nitrogen atmosphere, hexamethyldisilazane (1.0 g, 6.5 mmol) dissolved in 5 ml methylene chloride. After stirring at room temperature for about four hours, the solvent can be removed under aspirator pressure and the residue dissolved in 10 ml methanol. Upon stirring for about one hour, the solution can then be evaporated to dryness in vacuo to give the title compound.

EXAMPLE 35

3,4-Bis(methylsulfonyl)isothiazole-5-carbonitrile

To a suspension of 5.10 g (0.025 mole) of 3,4-bis(methylthio)isothiazole carbonitrile in 20 ml of acetic anhydride and 20 ml of glacial acetic acid was added, over 90 minutes with stirring, 11.90 g (0.105 mole) of 30% hydrogen peroxide. An ice bath was used intermittently throughout the addition to moderate the exothermic reaction. After 2 days at room temperature, the solid mass was diluted with water (500 ml) and filtered to afford 4.0 g of the title compound.

EXAMPLE 36

3,4-Dimethoxyisothiazole-5-carbonitrile

A mixture of the compound of Example 35 (3.95 g, 0.015 mol) and sodium carbonate (1.58 g, 0.015 mole) in 40 ml methanol can be stirred at reflux for 6 hours. On cooling, the mixture can be poured into water and the precipitate collected by suction filtration. Recrystallization of the solid from ethanol can give the pure title compound.

EXAMPLE 37

3,4-Dimethoxy-5-cyanoisothiazole-1-oxide

The title compound can be obtained by following the procedure of Example 29 using the compound of Example 36 in place of 3-methoxy-4-bromoisothiazole.

EXAMPLE 38

3,4-Dimethoxy-5-cyanoisothiazole-1,1-dioxide

The title compound can be obtained by following the procedure of Example 30 using the compound of Example 36 in place of 3-methoxy-4-bromoisothiazole.

EXAMPLE 39

3-[2-[5-Dimethylaminomethyl)-2-furanylmethylthio]ethyl]amino-4-amino-5-ethoxycarbonylisothiazole-1,1-dioxide To a solution of 510 mg (2.0 mmol) of the Example 5 compound in 4 ml dry acetonitrile under a nitrogen atmosphere there was added 440 mg (2.0 mmol) 2-[5-(dimethylaminomethyl)furanylmethylthio]ethylamine. A slight exothermicity was noted on mixing of the reactants. After 30 minutes at room temperature, the reaction was completed by tlc (Alumina 6F, 95:5 $CHCl_3:CH_3OH$). Upon evaporation of the solvent, the oily residue was triturated in a mixture cyclohexane:ethanol (10:1) from which there was obtained 760 mg of analytically pure title product, mp 90°–95°, as an ethanol solvate.

Anal. Calcd. for $C_{16}H_{24}N_4O_5S_2 \cdot C_2H_5OH$: N, 12.11; H, 6.54; S, 13.86. Found: N, 12.39; H, 6.44; S, 14.20.

EXAMPLE 40

3-N-[3-[3-(1-piperidinylmethyl)phenoxy]propyl]amino-4-amino-5-ethoxycarbonylisothiazole-1,1-dioxide Following the procedure of Example 39, 3-[3(1-piperidinylmethyl)phenoxy]propaneamine was reacted with the compound of Example 5 in acetonitrile to give the title compound as a crystalline hydrate, mp 111°–118°.

Anal. Calc'd for $C_{21}H_{30}N_4O_5S \cdot H_2O$: C, 53.83; N, 11.96; H, 6.88. Found: C, 53.91; N, 11.80; H, 7.04.

EXAMPLE 41

N-Trimethylsilyl-2-[5-(dimethylaminomethyl)-2-furanylmethylthio]ethyl amine

The dihydrochloride salt of 2-[5-(dimethylaminomethyl)-2-furanylmethylthio]ethylamine (10.0 g, 34.8 mmol) and 15 ml of hexamethyldisilazane were combined in 50 ml dry toluene and the mixture was stirred under vigorous reflux under a nitrogen atmosphere. After four hours, the toluene was distilled at atmospheric pressure, followed by hexamethyldisilazane at a slight vacuum and then the title product distilled as a yellow oil, bp 140°–145°/0.5 mm; 7.9 g. Further purification can be achieved by redistillation: bp 95°–96°/0.1 mm. $^1$H NMR (CDCl$_3$, no tetramethylsilane added) 6.05 (singlet-2 protons-furan), 3.64 (singlet -2 protons-furan-CH$_2$-S-), 3.38 (singlet -2 protons- furan-CH$_2$-N-), 2.90–2.40 (multiplet, 4 protons-CH$_2$CH$_2$-), 2.20 (singlet -6 protons- N(CH$_3$)2), 1.60 (singlet, 1 proton, NH) and 0.0 (singlet -9 protons Si(CH$_3$)3)

EXAMPLE 42

3-Amino-4-[2-(5-dimethylaminomethyl)-2-furanylmethylthio]ethylamino-5-ethoxycarbonylisothiazole-1,1-dioxide Under a nitrogen atmosphere, a solution of 900 mg (3.2 mmol) of the Example 4 compound in 20 ml dry tetrahydrofuran was stirred in a dry ice-acetonitrile bath (−35°) while being treated with a 3 ml solution containing 825 mg (3.2 mmol) of the trimethylsilylamine of Example 41 in tetrahydrofuran. The mixture was allowed to warm to 0°–15° and, after three hours, a tlc analysis (silica GF, 9:1 CHCl$_3$:C$_2$H$_5$OH) showed the reaction to be complete. An ammonia-tetrahydrofuran solution (7.0 ml of 0.465M, 3.2 mmol NH$_3$) was added dropwise and the resulting solution was stirred at ambient temperature for 18 hours. The white solid, which precipitated was collected and washed with ether to give 480 mg of the title product, mp 101°–103°.

Anal. Calcd. for $C_{16}H_{24}N_4O_5S$: C, 46.14: H, 5.80. Found: C, 46.16; H, 6.10.

EXAMPLE 43

3-N-[3-[3-(cyclopropylaminomethyl)phenoxy]propyl]amino-4-amino-5-carbamoylisothiazole-1,1-dioxide hydrochloride To an ice-cold solution of 1.53 g (7.0 mmol) of 3-ethoxy-4-amino-5-carbamoylisothiazole-1,1-dioxide in 10 ml acetonitrile there can be added dropwise, under nitrogen, a solution of 3-[3-(cyclopropylaminomethyl)phenoxy]propane amine (1.56 g, 7.0 mmol) in 10 ml acetonitrile. The mixture can then be stirred at room temperature for about two hours, the solvent evaporated in vacuo, and the residue chromatographed on silica gel using 1–2% ethanol in chloroform as elutant. Fractions containing the product-free base can then be combined and the solvent evaporated to give the title compound.

EXAMPLE 44

3-N-[2-[6-(4-morpholinylmethyl)-2-benzofuranylmethylthio]ethyl]amino-4-amino-5-ethoxycarbonylisothiazole-1,1-dioxide The title compound can be obtained by reaction of 4.0 mmol each of 2-[[6-(4-morpholinylmethyl)-2-benzofuranyl]methylthio]ethyl amine and the compound of Example 5 in 8 ml of acetonitrile. The pure product can then be crystallized from the reaction solution and collected by filtration.

EXAMPLE 45

3-N-[2-[5-(dimethylaminomethyl)-2-furanylmethylthio]ethyl]amino-4-amino-5-N-[(2-dimethylamino)-ethyl]-carbamoylisothiazole-1-oxide Following the procedure in Example 39 with the reagent of Example 26 and 2-[(5-dimethylaminomethyl-2-furanyl)methylthio)ethylamine, the pure title compound can be obtained.

EXAMPLE 46

3-N-[2-[(4-methyl-5-oxazolyl)methylthio)ethylamino-4-amino-5-N-[2-hydroxyethyl]carbamoylisothiazole-1-oxide The title compound can be obtained as described in Example 39 using the product of Example 27 and 2-[(4-methyl-5-oxazolyl)methylthio]-ethane amine.

EXAMPLE 47

3-N-[2-[[6-(morpholinylmethyl)-2-benzofuranyl]methylthio]ethyl]amino-4-amino-5-N-[2-hydroxyethyl]-carbamoylisothiazole-1-oxide The title compound can be obtained as described in Example 39 using the product from Example 27 and 2-[[6-(4-morpholinylmethyl)-2-benzofuranyl]methylthio]-ethyl amine.

EXAMPLE 48

3-N-[2-[5-(dimethylaminomethyl)-2-furanylmethylthio]ethyl]-amino-4-amino-5-methylisothiazole-1,1-dioxide The title compound can be obtained as described in Example 39 using the compound of Example 28 in place of that of Example 5.

EXAMPLE 49

3-N-[2-[(2-guanidino-4-thiazolyl)methylthio]ethyl]amino-4-amino-5-methylisothiazole-1,1-dioxide The title compound can be obtained as described in Example 39 using equimolar amounts of 2-[(2-guanidino-4-thiazolyl)methylthio]ethanamine and the product of Example 28.

EXAMPLE 50

3-N-[2-[(4-methyl-5-imidazolyl)methylthio]ethyl]amino-4-methoxy isothiazole-1-oxide To a solution of 1.61 g (0.01 mol) of the Example 31 compound in 20 ml dry tetrahydrofuran at −20° under a nitrogen atmosphere, there can be added 1.71 g (0.01 mol) of 2-[(4-methyl-5-imidazolyl)methylthio]ethylamine dissolved in 10 ml dry tetrahydrofuran. The mixture can then be allowed to warm to room temperature and, after about 18 hours, can be concentrated to one-half volume to afford the title compound as a precipitate.

EXAMPLE 51

3-N-[2-[(4-methyl-5-imidazolyl)-methylthio]e-thylamino4-methylamino-isothiazole-1-oxide hydrochloride A solution of anhydrous methylamine in tetrahydrofuran (10 ml, 0.55M) can be added dropwise to a solution of the Example 50 compound (1.63 g, 5.5 mmol) dissolved in 20 ml dry tetrahydrofuran at about 0° under a nitrogen atmosphere. When the addition is complete, the ice bath can be removed and the solution slowly warmed t room temperature. After about 24 hours, the solvent can be evaporated in vacuo and the crude oily residue can be chromatographed using silica gel flash chromatography, eluting with 1-5% methanol in chloroform. The product fractions can then be combined, the solvent evaporated in vacuo, and the residual gum dissolved in a mixture of ethanol-tetrahydrofuran. Addition of 0.45 ml of concentrated hydrochloric acid should then precipitate the title compound.

EXAMPLE 52

3-Amino-4-N-[3-[3-(4-morpholinylmethyl)phenoxy]-propyl]aminoisothiazole-1,1-dioxide By the method of Example 42, using equimolar amounts of 3-[3-(4-morpholinylmethyl)phenoxy]-propanamine and the compound of Example 34, the title compound can be obtained.

EXAMPLE 53

α-tert-Butyloxycarbonyl-α-tosyloximinoacetonitrile

A mixture of tert-butylcyanoacetate (5.0 g, 0.035 mole), sodium acetate (3.4 g, 0.042 mole), and sodium nitrite (2.9 g, 0.042 mole) in 15 ml water was stirred in an ice bath during dropwise addition of acetic acid (2.6 ml, 0.045 mole). Stirring was then continued at room temperature overnight. A yellow waxy solid was collected (4.2 g) which contained unreacted tert-butyl cyanoacetate by pmr. This material was recycled with fresh sodium nitrite (1.2 g, 0.0175 mole), sodium acetate (1.4 g, 0.0175 mole) and acetic acid (1.0 ml, 0.018 mole). The waxy solid which resulted, (a mixture of (α-oximino)tert-butyl cyanoacetate and the sodium salt thereof) was washed with water and dried. The solid (3.2 g, approximately 0.0179 mole) was dissolved in 15 ml dry pyridine and to this solution at −5° C. there was added protionwise p-toluenesulfonyl chloride (3.4 g, 0.0179 mole). After one hour, the suspension was poured into 100 ml ice water and the solid which crystallized was collected and dried: 5.2 g of the title compound, mp 101°-102° C.

EXAMPLE 54

3-tert-Butyloxycarbonyl-4-amino-5-ethoxycarbonylisothiazole

Pyridine (1.62 ml, 0.020 mole) was added dropwise to a solution of 5.15 g (0.016 mole) (α-tosyloximino)tert-butyl cyanoacetate and 2.66 ml 0.024 mole) ethyl-2-mercapto acetate in 6 ml absolute ethanol at such a rate as to maintain a reaction temperature of 35°-40°. When the addition was completed, the solution was stirred one hour before pouring it into 80 ml ice water. Ether extraction afforded 2-cyano-2-tert-butyloxycarbonylmethylthioimino acetic acid ethyl ester as an oil. This material was cyclized directly by dissolving it in 50 ml acetonitrile and treating the solution with 2.6 g 0.026 mole) triethylamine under a nitrogen atmosphere. After 1.5 hours, the mixture was concentrated in vacuo to ⅓ its original volume, the residue poured into water and the product extracted into ether. The dried ($Na_2SO_4$) ether extract was evaporated to an oil which was chromatographed over silica gel (chloroform elution). The title compound was obtained as an oily solid in 87% yield (3.8 g). Washing the solid with an ether-hexane mixture afforded analytically pure material, mp 68°-69°.

EXAMPLE 55

3-Carboxylic acid-4-amino-5-ethoxycarbonylisothiazole

Nine grams (0.033 mole) of the diester of Example 54 was dissolved in 30 ml trifluoroacetic acid and the solution allowed to stand at room temperature for two hours. The 7.5 g of yellow solid that remained upon evaporation of the solvent had a mp 144°-147°. Recrystallization of this crude 3-carboxylic acid-4-amino-5-ethoxycarbonylisothiazole from n-butylchloride afforded analytically pure material, mp 146°-148°.

EXAMPLE 56

3-Hydroxymethyl-4-amino-5-ethoxycarbonylisothiazole

A solution containing 6.0 g (0.0277 mole) of 3-carboxylic acid 4-amino-5-ethoxycarbonylisothiazole in 60 ml of dry tetrahydrofuran was stirred at -10° to 0° under a nitrogen atmosphere while a solution of borane in tetrahydrofuran (83 ml, 1N) was added dropwise. The mixture was allowed to warm to room temperature, then stirred at reflux for two hours before chilling in an ice bath and quenching with dropwise addition of 1N HCl. The resultant mixture was concentrated on a rotary evaporator to a semisolid which was then extracted into ethyl acetate. Upon washing the organic phase with water, aqueous sodium bicarbonate, then brine, the ethyl acetate was dried (sodium sulfate), filtered, and evaporated in vacuo to give the title compound as a solid, mp 82°-85° C. An analytical sample, mp 84°-86° was prepared by recrystallization from n-butylchloride.

EXAMPLE 57

4-Amino-5-ethoxycarbonylisothiazolin-3-one-1-oxide

To a solution of 3-hydroxymethyl-4-amino-5ethoxycarbonylisothiazole (2.0 g, 0.010 mole) in 40 ml acetic acid-water (28:12) was added 0.10 ml perchloric acid (70%) and the solution was warmed to 40°. Over ten minutes there was added dropwise 2.8 ml 30% hydrogen peroxide solution (0.025 mole) dissolved in 10 ml 70% aqueous acetic acid. After one hour, the reaction temperature was raised to 60° and the solution stirred for 24 hours at this temperature. A test with potassium iodide/starch paper revealed no peroxide left. The solution was then cooled, poured onto crushed ice, and extracted with methylene chloride to remove any unreacted starting material. The aqueous phase was then treated with sodium chloride and extracted with ethyl acetate (4×50 ml). The combined ethyl acetate extracts were dried over sodium sulfate before concentrating in vacuo to an oily solid which was triturated with ethanol to afford the title compound, mp 197°-198°.

EXAMPLE 58

3-Ethoxy-4-amino-5-ethoxycarbonylisothiazole-1-oxide

A mixture of 1.55 g (7.6 mmole) of 4-amino-5-ethoxycarbonylisothiazolin-3-one-1-oxide, 1.38 g (10.0 mmole) of potassium carbonate, and 0.64 ml (8.0 mmole) of ethyl iodide in 6 ml dimethylsulfoxide was stirred at room temperature for 18 hours. The suspension was then poured onto crushed ice and extracted with ethyl acetate (3×30 ml). The combined organic phases were washed one time each with ice water and brine, then dried over sodium sulfate. The title compound, which was obtained upon removal of the solvent, was identical to the product of Example 7.

EXAMPLE 59

3-[2-[5-(Dimethylaminomethyl)-2-furanylmethylthio]ethyl]amino-4-amino-5-ethoxycarbonylisothiazole-1-oxide The title compound was obtained by effecting a tetrahydrofuran solution of equimolar amounts of 2-[5-(dimethylaminomethyl)furanylmethylthio]ethylamine and the compound of Example 58 and allowing the mixture to stir at ambient temperature under nitrogen for 48 hours. Removal of the solvent in vacuo afforded the title compound as a crystalline solid which was recrystallized from ethanol and was identical to the product of Example 70.

EXAMPLE 60

Methyl N-(benzylsulfonyl)oxamate

A mixture of benzylsulfonamide (16.7 g, 0.0975 mole) and methyloxalylchloride (38 ml, 0.41 mol) was heated at 100°–120° C. for 2 hours. Upon evaporation, there was obtained the title compound, 20.6 g, mp 119°–124° C.

EXAMPLE 61

3-[2-[5-(Dimethylaminomethyl)-2-furanylmethylthio]ethyl]amino-4-amino-5-phenylisothiazole-1,1-dioxide

Step A Disodium salt of 3,4-dihydroxy-5-phenylisothiazole-1,1-dioxide

A solution of sodium tert-butoxide was prepared by adding dropwise, under nitrogen, a solution of tert-butanol (7.2 ml, 0.078 mol) in dry N,N-dimethylformamide (15 ml) to a stirred mixture of sodium hydride (3.7 g of a 50% dispersion in mineral oil, 0.078 mol) in dry N,N-dimethylformamide (10 ml). External cooling was required to maintain a reaction temperature of 15° to 25°. The mixture was then stirred at 25° until gas evolution ceased (20–30 minutes). To this mixture, there was added dropwise a solution of methyl N-(benzylsulfonyl)oxamate (10.0 g, 0.039 mol) in N,N-dimethylformamide (25 ml), maintaining a reaction temperature of 15° to 25° C. The solution was then stirred overnight at room temperature. Evaporation of the solvent at 55°/0.1 mm Hg left the title compound as a solid.

Step B Disilver Salt of 3,4-dihydroxv-5-phenylisothiazole-1,1-dioxide

The product from Step A (16.6 g, 0.062 mol) was dissolved in 250 ml water, the solution filtered, and the filtrate treated with 21.2 g (0.125 mol) silver nitrate dissolved in 50 ml water. The mixture was stirred under nitrogen for 24 hours and the product collected by filtration. The solid title compound was dried at 100° in vacuo for 24 hours: yield, 24.8 g (91%).

Step C 3,4-Diethoxy-5-phenylisothiazole-1,1-dioxide

A suspension of the disilver salt from Step B (24.3 g, 0.055 mol) in 70 ml dry acetonitrile was stirred under nitrogen in a 60° oil bath while a soluion of iodoethane (19.5 g, 0.125 mol) in 30 ml dry acetonitrile was added dropwise. When the addition was complete the heat was removed and the mixture allowed to stir at ambient temperature for two days. Filtration of the mixture through Celite, followed by evaporation of the clear filtrate gave an oily solid (13 g, 85%) which was a mixture of the title compound and its isomer, 2-ethyl-4-ethoxy-5-phenyl-3-isothiazolinone, in a 35:65 ratio. Chromatography on silica gel eluting with ethyl acetate:hexane (1:4) gave 3.3 g of pure title compound, m.p. 133°–134°.

Step D
3-N-[2-[5-(Dimethylaminomethyl)-2-furanylmethylthio]ethyl]amino-4-ethoxy-5-phenylisothiazo-1,1-dioxide A solution of the compound from Step C (1.2 g, 4.2 mmol) in 25 mL acetonitrile was treated with 2-[5-(dimethylaminomethyl)furanylmethylthio]ethylamine (0.90 g, 4.2 mmol). After stirring under nitrogen at ambient temperature for 2 hours, the solvent was evaporated in vacuo to give an oil which crystallized from ethanol-ethyl ether: 1.5 g (81%) of the title compound, mp 92°–98°.

Step E
3-N-[2-[5-(Dimethylaminomethyl)-2-furanylmethylthio]ethyl]amino-4-amino-5-phenylisothiazole-1,1-dioxide A 90 mL capacity glass pressure bottle was charged with 1.0 g (2.2 mmol) of the compound of Step D. The bottle was immersed in a dry ice-acetone bath and ammonia gas (ca. 3 mL) was condensed in the bottle. After sealing the bottle with a pressure valve, the cooling bath was removed and the solution stirred at ambient temperature for 18 hours. The residue left after venting off the reaction vessel and evaporation of excess ammonia was taken up in ethyl acetate and the solution washed with brine. The organic phase was concentrated in vacuo and the residue chromatographed over silica gel, eluting with chloroform saturated with ammonia (0 to 10% methanol). The title compound, 430 mg, was obtained as tlc homogeneous white solid which was recrystallized from acetonitrile. The pure compound was an amorphous hemihydrate, mp 74°–77°.

EXAMPLE 62

3-N-[2-[(2-Guanidino-5-methyl-4-thiazolyl)methylthio]ethyl]amino-4-amino-5-ethoxycarbonylisothiazole-1,1-dioxide tetrahydrofuran solvate hemihydrate

Step A 4,5-Dimethyl-2-guanidinothiazole hydrobromide

Amidinothiourea hydrobromide (15.4 g, 0.10 mol) was slurried in 100 ml of ice water and the stirred suspension treated with 7.0 ml of concentrated aqueous ammonia. The mixture was stirred for 30 minutes at 0°–5° and filtered to give 10.8 g (0.091 mol) of amidinothiourea. This was slurried in a solution of 13.5 g (0.089 mol) of 3-bromo-2-butanone in 100 ml of acetone and the mixture was kept at room temperature overnight (a mild exotherm gave a clear solution which deposited crystals of the title compound). The title compound, 17 g, mp 268°–269°, was collected by suction.

Step B 4-Bromomethyl-5-methyl-2-quanidinothiazole hydrobromide

A solution of the product from Step A (5.0 g, 0.020 mol) in 25 ml of trifluroacetic acid was heated to reflux and treated with bromine added, by way of a teflon tube, below the surface of the refluxing mixture. A total of 2.2 ml of bromine was added during 6 hours reflux after which an nmr spectrum showed complete conversion of the methyl signal of starting material at 2.5 to a $CH_2$ signal at 4.53. The mixture was concentrated in vacuo and the solvent replaced by isopropanol saturated with hydrogen bromide. The crude product, which crystallized (3.9 g), was recrystallized from glacial acetic acid to give the pure title compound (2.8 g, 42%), mp 188°–188.5° C.

Step C
2-[(2-Guanidino-5-methyl-4-thiazolyl))methylthio]ethylamine maleate To a stirred solution of cysteamine hydrochloride (1.7 g, 0.017 mol) in 25 ml of methanol was added a solution of 1.7 g (0.031 mol) of sodium methoxide in 15 ml of methanol under nitrogen at 0° to −15° C. To the resulting mixture there was added a solution of 2.5 g (0.0075 mol) of the product from Step B in 40 ml of methanol at 0° C. The resulting mixture was warmed to rom temperature during 4 hours and then concentrated under vacuum. The residue was partitioned between aqueous sodium hydroxide (saturate with sodium chloride) and methylene chloride. The methylene chloride extract was dried (sodium sulfate), filtered and concentrated under vacuum to an oil which was crystallized from acetonitrile to give the crude title amine. This was boiled in 50 ml of acetonitrile and the solution filtered through diatomaceous earth. The filtrate was treated with a solution of 0.065 g of maleic acid in 25 ml of acetonitrile and the title salt, which crystallized, was collected by suction; yield 1.4 g, mp 232°–234° C.

Step D 3-N-[2-[(2-Guanidino-5-methyl -4-thiazolyl)methylthio]ethyl]amino-4-amino-5-ethoxycarbonylisothiazole-1,1-dioxide tetrahydrofuran solvate hemihydrate The salt from Step C (1.3 g, 0.0036 mol) was partitioned between a mixture of 2 ml of 10N sodium hydroxide and 3 ml of 5% ethanol-methylene chloride. The layers were separated and the extraction repeated. The combined methylene chloride layers were dried (sodium sulfate), filtered, and concentrated under vacuum. The residue was dissolved in 20 ml of dry tetrahydrofuran and the cloudy solution filtered through diatomaceous earth into a solution of 3-ethoxy-4-amino-5-ethoxy carbonylisothiazole-1,1-dioxide in 20 ml of dry tetrahydrofuran. The resulting clear solution was stirred overnight at room temperature and the precipitated 3-N-[2-[(2-guanidino-5-methyl-4-thiazolylmethylthio]ethyl]amino-4-amino-5-ethoxycarbonylisothiazole-1,1dioxide tetrahydrofuran solvate hemihydrate collected by suction: mp 150°–152° C. (dec).

EXAMPLE 63
3-N-[2-[(2-Guanidino-4-thiazolyl)methylthio]ethyl]amino-4-amino-5-ethoxycarbonylisothiazole-1,1dioxide hydrate To the suspension of 3-ethoxy-4-amino-5-ethoxycarbonylisothiazole-1,1-dioxide (0.74 g, 0.0030 mol) in ethanol (3 ml) there was added a solution of 2-[(2-guanidino-4-thiazolyl)methythio]ethylamine (0.69 g, 0.0030 mol) in ethanol (4 ml) resulting in a clear yellow solution. A gum was deposited after 30 min. After 24 hours, the mixture was concentrated to dryness in vacuo and the residue was chromatographed on a column of E. Merck silica gel 60. From the fraction eluted with 10% methanol/chloroform followed by 20% and 30% methanol/chloroform, there was obtained 1.12 g glassy solid. The glass was triturated with hot acetonitrile and the solid filtered and dried to give 0.80 g glassy solid. After recrystallization from isopropanol followed by recrystallization from methanol 0.35 g (27%) of the title product was obtained, mp 201°–203°. TLC (30% methanol/chloroform, silica): Rf=0.61.

Calc'd for $C_{13}H_{19}N_7O_4S_3 \cdot H_2H_{O\cdot N}$, 21.55; C, 34.57; H, 4.33. Found: N, 21.72; C, 34.58; H, 4.69.

EXAMPLE 64
3-Amino-4-[2-(5-dimethylaminomethyl)-2-furanylmethylthio]ethyl]amino-5-cyano-isothiazole-1,1-dioxide To a suspension of 3-amino-4-ethoxy-5-cyanoisothiazole-1,1-dioxide (0.60 g, 0.0030 mol) in acetonitrile (20 ml) there was added dropwise a solution of 2-[5-(dimethylaminomethyl)furanylthio]ethylamine (0.64 g, 0.0030 mol) in acetonitrile (3 ml) to give an orange solution. A precipitate formed within 30 minutes and the reaction was completed within 120 minutes by TLC. The precipitate was filtered off, washed with ether, and dried to give 0.85 g (77%) of the title compound; mp 166.5°–167.5° (d) TLC (20% methanol/chloroform, silica): Rf=0.30.

EXAMPLE 65
3-N-[2-(5-Dimethylaminomethyl-2-furanylmethylthio)ethyl]amino-4-amino-5-cyanoisothiazole-1,1-dioxide·½CH$_3$CN To a solution of 3,4-diethoxy-5-cyanoisothiazole-1,1-dioxide (1.25 g, 0.0050 mol) in acetonitrile (15 ml) cooled in an ice/methanol bath there was added dropwise a solution of 2-[5H-(dimethylaminomethyl)-furanylthio]ethylamine (1.07 g, 0.0050 mol) in acetonitrile (5 ml). The solution was warmed to ambient temperature and stirred for 60 min. at which time no further reaction was noted by TLC. Dry ammonia was then bubbled into the solution cooled in an ice bath for 10 minutes. The solution was then warmed to ambient temperature and stirred for 60 minutes. The solution was concentrated to dryness in vacuo to give an orange glass which was triturated with acetonitrile to give a solid. The mixture was cooled in an ice bath and the solid filtered off to give crude product, mp 137°–139°. The crude product (1.48 g) was dissolved in methanol and concentrated to dryness. The residue was triturated with acetonitrile, filtered off, and dried to obtain 1.29 g of product; mp 142°–143° (d). TLC (20% methanol/chloroform, silica): Rf=0.38.

Calc'd for $C_{14}H_{19H}N_5O_3S_2 \cdot \frac{1}{2}CH_3CN$: 19.76; C, 46.19; H, 5.30. Found: N, 19.78; C, 46.22; H, 5.32.

EXAMPLE 66
3-[2-[(5-Dimethylaminomethyl-2-furanyl)methylthio]ethyl]amino-4-amino-5-methylsulfonylisothiazole-1-oxide To a solution of 2-[(5-dimethylaminomethyl-2furanyl)methylthio]ethylamine (440 mg, 2 mmol) in acetonitrile (6 ml) there was added 3-ethoxy-4-amino-5-methylsulfonylisothiazole-1-oxide (480 mg, 2 mmol). This mixture was stirred under a nitrogen atmosphere for 15 hours as product slowly crystallized out. Precipitate was collected by filtration, washed with acetonitrile, diethyl ether and air dried to give 650 mg, of title compound, mp 134°–137°.

EXAMPLE 67

3-[2-[(5-Dimethylaminomethyl-2-furanyl)methylthio]ethyl]amino-4-amino-5-methylsulfonylisothiazole-1,1-dioxide To a solution of 2-[(5-dimethylaminomethyl-2furanyl)methylthio]ethylamine (0.66 g, 3.08 mmol) in acetonitrile (5 ml) under a nitrogen atmosphere there was added solid 3-ethoxy-4-amino-5-methylsulfonylisothiazole-1,1-dioxide (0.77 g, 3.01 mmol) to give an immediate solution and exothermic reaction. After ¼ hour, the product began to crystallize and after stirring for 15 hours, was collected by filtration (1.2 g). The title compound was recrystallized by dissolving in hot methanol and diluting with several volumes of ether (1.0 g), mp 187°–189°.

EXAMPLE 68

3-Amino-4-[2-[(5-dimethylaminomethyl-2-furanyl)methylthio]ethyl]amino-5-dimethylcarbamylisothiazole-1,1-dioxide

Step A 3-amino-4-[2-[(5-dimethylaminomethyl-2-furanyl)methylthio]ethylamino]-4-ethoxy-5-dimethylcarbamyl-4,5-dihydroisothiazole-1,1-dioxide To a solution of 3-amino-4-ethoxy-5-dimethylcarbamylisothiazole-1,1-dioxide (0.62 g, 2.5 mmol) in acetonitrile (6 ml) there was added dropwise a solution of 2-[(5-dimethylaminomethyl-2-furanyl)methylthio]ethylamine (0.55 g, 2.6 mmol) in acetonitrile (5 ml). After stirring at ambient temperature for (16–20 hours, precipitated material was collected to give 0.9 g of title compound, mp 143°–144°.

Step B

3-Amino-4-[2-[(5-dimethylaminomethyl-2-furanyl)methylthio]ethyl]amino-5-dimethylcarbamylisothiazole-1,1-dioxide The compound from Step A was dissolved (0.9 g, 1.9 mmol) in acetonitrile (20 ml) and methylene chloride (10 ml) and silica gel added in portions (4.0 g) until all of compound was adsorbed on silica gel. Then, solvent was evaporated, coated silica gel was packed on top of silica gel column, and the title compound eluted with 7–8% methanol/chloroform to give 0.4 g of a glassy solid.

EXAMPLE 69

3-[2-[(5-Dimethylaminomethyl-2-furanyl)methylthio]ethyl]amino-4-amino-5-N,N-dimethylcarbamoylisothiazole-1,1-dioxide

Step A

3-[2-[(5-Dimethylaminomethyl-2-furanyl)methylthio]ethyl]amino-4-ethoxy-5-dimethylcarbamylisothiazole-1,1-dioxide To a solution of 60% pure 3,4-diethoxy-5-dimethylcarbamylisothiazole-1,1-dioxide (1.7 g from Example 10, Step C) in acetonitrile (7 ml) there was added dropwise a solution of 2-[(5-dimethylaminomethyl-2-furanyl)methylthio]ethylamine (0.81 g, 3.8 mmol) in acetonitrile (5 ml). After stirring at ambient temperature for 1–2 hours, solvent was evaporated and the residue chromatographed on silica gel, eluting with 4% methanol/chloroform, to give 1.4 g of purified oily title compound.

Step B

3-[2-[(5-Dimethylaminomethyl-2-furanyl)methylthio]ethyl]amino-4-amino-5-dimethylcarbamylisothiazole-1,1-dioxide Into a solution of 3-[2-[(5-dimethylaminomethyl-2-furanyl)methylthio]ethyl]amino-4-ethoxy-5-dimethylcarbamylisothiazole-1,1-dioxide (1.4 g, 3.2 mmol) in acetonitrile (12 ml) warmed at 65° C., ammonia gas was slowly bubbled over a 1–2 hour period. Solvent was evaporated, residue chromatographed on silica gel eluting with 3–5% methanol/chloroform to give 0.96 g of title compound which could be crystallized from nitromethane/ether, mp 101°–104°.

EXAMPLE 70

3-[2-[5-Dimethylaminomethyl)-2-furanylmethylthio]ethyl]amino-4-amino-5-ethoxycarbonylisothiazole-1-oxide 3-Ethoxy-4-amino-5-ethoxycarbonylisothiazole-1-oxide (0.5 g, 2.15 mmol) was stirred in 3 ml of dry acetonitrile under nitrogen atmosphere and 2-[5-(dimethylaminomethyl)furanylmethylthio]ethylamine (0.46 g, 2.15 mmol) in 2 ml of dry acetonitrile was added dropwise over five minutes. Stirring was continued at ambient temperature overnight. The product precipitated to give 0.8 g of the title compound as a white solid, mp 88°–94°.

EXAMPLE 71

3-[2-[(5-Dimethylaminomethyl-2-furanylmethylthio]ethyl]amino-4-amino-5-carbamoylisothiazole-1-oxide

Step A

3-Ethoxy-4-bromo-5-(trimethylsilyloxycarbonyl) isothiazole-1-oxide

3-Ethoxy-4-bromo-5-carboxyisothiazole-1-oxide (4.02 g, 0.015 mol) was silylated with trimethylchlorosilane in 10% excess (1.79 g, 0.0165 mol) in an anhydrous inert solvent (dry acetonitrile) using the standard literature silylation procedure. Solvent and excess reagent were removed in vacuo and the crude silyl ester was used without further purification.

Step B

3-[2-[5-(Dimethylaminomethyl)-2-furanylmethylthio]ethyl]amino-4-amino-5-carboxyisothiazole-1-oxide 3-Ethoxy-4-bromo-5-(trimethylsilyloxycarbonyl) isothiazole-1-oxide (0.68 g, 2.0 mmol) was dissolved in 3 ml of dry acetonitrile and aminated by the careful addition of anhydrous ammonia in acetonitrile added at ice bath temperature. When no more starting material remained (by TLC), an equivalent of 2-[5-(dimethylaminomethyl-2-furanylmethylthio]ethylamine (0.43 g, 2.0 mmol) was added dropwise and the reaction mixture stirred under nitrogen atmosphere for 24 hours. The solvent was then removed in vacuo and the residue heated at reflux in 10 ml of methanol for ten minutes. Removal of the solvent in vacuo gave the crude title compound which was purified by crystallization.

Step C
3-[2-[5-(Dimethylaminomethyl)-2-furanylmethylthio]-ethylamino]-4-amino-5-carbamoylisothiazole-1-oxide The Woodward's ester of 3-[2-[5-(dimethylaminomethyl)-2-furanylinethylthio]ethyl]amino-4-amino-5-carboxyisothiazole-1-oxide was prepared from the carboxylic acid (0.37 g, 1.0 mmol) by reaction with N-t-butyl-5-methylisoxazolium perchlorate (0.24 g, 1.0 mmol) in 3 ml of dry DMF using literature methodology. Reaction of the "active ester" with excess anhydrous ammonia in absolute ethanol gave the amide title compound.

EXAMPLE 72
3-[2-[5-(Dimethylaminomethyl)-2-furanylmethylthio]-ethyl]amino-4-amino-5-carbamoylisothiazole-1,1-dioxide

Step A
3-Ethoxy-4-bromo-5-carboxyisothiazole-1,1dioxide

3-Ethoxy-4-bromo-5-carbamoylisothiazole-1,1-dioxide (283 mg, 1.0 mmol) was dissolved in 2 ml of trifluoroacetic acid and sodium nitrite (138 mg, 2.0 mmol) was added in small portions over a two minute period with stirring. Stirring was continued for two minutes at room temperature and then the solvent was removed in vacuo. The residual gum was stirred in ice water and the solid title compound was quickly filtered and dried in vacuo.

Step B
3-Ethoxy-4-bromo-5-(trimethylsilyloxycarbonyl) isothiazole-1,1-dioxide 3-Ethoxy-4-bromo-5-carboxyisothiazole-1,1-dioxide (5.68 g, 0.02 mol) was silylated in acetonitrile using the procedure described for the preparation of the 1-oxide analog in Example 71. Standard work up gave the title compound.

Step C
3-[2-[5-(Dimethylaminomethyl)-2-furanylmethylthio]-ethyl]amino-4-amino-5-carboxyisothiazole-1,1-dioxide 3-Ethoxy-4-bromo-5-(trimethylsilyloxycarbonyl) isothiazole-1,1-dioxide (0.89 g, 2.5 mmol) was aminated in 5 ml of dry acetonitrile according to the procedure used for the 1-oxide analog in Example 71. Addition of an equivalent of 2-[5-(dimethylaminomethyl-2-furanylmethylthio]ethylamine (0.54 g, 2.0 mmol) followed by hydrolysis of the silyl ester as in Example 71 gave the title compound. Purification was accomplished by chromatography on silica gel.

Step D
3-[2-[5-(Dimethylaminomethyl)-2-furanylmethylthio]-ethyl]amino-4-amino-5-carbamoylisothia-1,1-dioxide The Woodward's ester of 3-[2-[5-(dimethylaminomethyl)-2-furanylmethylthio]ethyl]amino-4-amino-5-carboxyisothiazole-1,1-dioxide was prepared from the carboxylic acid (0.39 g, 1.0 mmol) by reaction with N-t-butyl-5-methylisoxazolium perchlorate to (0.24 g, 1.0 mmol) as in Example 71 for the 1-oxide analog. Conversion of the "active ester" to the carboxamide was accomplished with excess ammonia as in Example 71.

EXAMPLE 73
3-Amino-4-[2-[5-(dimethylaminomethyl)-2-furanylmethylthio]ethyl]amino-5-carbamoylisothiazole-1,1-dioxide

Step A
3-Ethoxy-4-phenoxy-5-carbamoylisothiazole-1,1-dioxide

A solution of 3-ethoxy-4-bromo-5-carbamoylisothiazole-1,1-dioxide (283 mg, 1.0 mmol) in 15 ml of dry THF was cooled in ice and stirred as thallous phenoxide (279 mg, 1.0 mmol) was added in small portions over ten minutes. The mixture was stirred for 1½ hours at ambient temperature. The resulting suspension was cooled in ice and filtered. The solid was purified by chromatography on silica gel followed by recrystallization from chlorofrom. The pure white solid melts at 183°–186° C.

Step B
3-Amino-4[2-[5-(dimethylaminomethyl)-2-furanylmethylthio]ethyl]amino-5-carbamoylisothiazole-1,1-dioxide 3-Ethoxy-4-phenoxy-5-carbamoylisothiazole-1,1-dioxide (0.46 g, 1.55 mmol) in 5 ml of THF was stirred at ice bath temperature while N-trimethylsilyl 2-[5-(dimethylaminomethyl)-2-furanylmethylthio]ethylamine (0.44 g, 1.55 mmol) in 2 ml of THF was added dropwise over 20 minutes. After an additional 10 minutes, the solution was concentrated to dryness in vacuo. The residual solid was taken up in 10 ml of THF and 10 ml of chloroform and was saturated with anhydrous ammonia. This mixture was stirred at ambient temperature for 1–1/2 hours then the solvent was removed in vacuo. The crude yellow solid was purified by chromatography on silica gel and recrystallized from acetonitrile. The yellow solid melts at 128°–130° C.

EXAMPLE 74
3-N-[2-[5-(Dimethylaminomethyl)-2-furanylmethylthio]ethyl]amino-4-amino-5-benzyloxycarbonylisothiazole-1,1-dioxide Step A  3-Ethoxy-4-bromoisothiazole-5-carboxylic acid potassium salt To a solution of 3-ethoxy-4-bromoisothiazole-5-carboxylic acid (2.02 g, 0.0080 mol) in methanol (8 ml) there was added a solution of potassium hydroxide (0.45 g, 0.0080 mol) in methanol (8 ml). The resulting solution was stirred at ambient temperature for 10 minutes and concentrated to dryness in vacuo. The residue was dried (60°, 0.1 mm) to give 4-bromo-3-ethoxyisothiazole-5-carboxylic acid potassium salt (2.24 g, 97%, mp 265°–268° (d)).

Step B
3-Ethoxy-4-bromo-5-benzyloxycarbonylisothiazole

To a suspension of 3-ethoxy-4-bromoisothiazole-5-carboxylic acid potassium salt (2.32 g, 0.0080 mol) in dry DMF (13 ml) there was added benzyl bromide (1.10 ml, 0.0093 mol). All solids dissolved and a fine precipitate formed. After 90 minutes, the mixture was filtered and the filtrate poured into ice-water (40 ml). The mixture was extracted with ether (2 × 50 ml). The combined ether extracts were washed with saturated sodium bicarbonate solution (15 ml), dried over sodium sulfate, and filtered. Hexane (100 ml) was added to the filtrate causing crystallization of the product. The mixture was cooled to 5° and the crystals filtered off and dried to give the product (2.06 g, 75%, mp 48°–49.5°). TLC (2% methanol/chloroform, silica): Rf=0.90.

Calc'd for $C_{13}H_{12}BrNO_3S$: N, 4.09; C, 45.62; H, 3.53. Found: N, 3.92; C, 45.44; H, 3.51.

Step C
3-Ethoxy-4-bromo-5-benzyloxycarbonylisothiazole-1,1-dioxide

To cold methylene chloride (15 ml) there was added 90% hydrogen peroxide (0.51 g, 0.0134 mol). To the resulting suspension, cooled in an ice-bath, was added, dropwise with stirring, trifluoroacetic anhydride (2.07 ml, 0.0147 mol) at 7°–10° over 20 minutes. The resulting solution was warmed to 15°, stirred for 15 minutes, and then cooled in an ice-bath. The solution of 3-ethoxy-4-bromoisothiazole-5-carboxylic benzyl ester (2.02 g, 0.0059 mol) in methylene chloride (6 ml) was added dropwise at 3°–6° over 20 minutes. The solution was stirred at 10°–15° for 2 hours and then at ambient temperature for 6 hours. The solution was concentrated in vacuo at ambient temperature to a small volume (5 ml) and chromatographed on a column of E. Merck silica gel 60 eluted with chloroform. A white solid (1.95 g) was obtained which was recrystallized from n-butyl chloride/hexane (1:1) to give the product (1.80 g, 81%, mp 123°–124°). TLC (chloroform, silica): Rf=0.71.

Calc'd for $C_{13}H_{12}BrNO_5S$: N, 3.74; C, 41.72; H, 3.23. Found: N, 3.72; C, 41.90; H, 3.17.

Step D
3-Ethoxy-4-amino-5-benzyloxycarbonylisothiazole-1,1-dioxide

To a suspension of 3-ethoxy-4-bromo-5-benzyloxycarbonylisothiazole-1,1-dioxide (1.50 g, 0.0040 mol) in acetonitrile (6 ml) there was added hexamethyldisilazane (0.91 ml, 0.0043 mol). The mixture was heated at 70° for 3.5 hours. Additional hexamethyldisilazane (0.21 ml, 0.0010 mol) was added and the solution stirred at 70° for 1.5 hours. The mixture was then concentrated to dryness in vacuo and the residue dissolved in ethanol (50 ml) and stirred for 15 minutes. The solution was concentrated to dryness in vacuo and the residue recrystallized from ethanol to give the title product (0.95 g, 77%, mp 149°–151°).

The mother liquors were concentrated to dryness and the residue placed in acetonitrile (3 ml). Hexamethyldisilazane (0.21 ml, 0.0010 mol) was added and the solution heated at 70° for 1.5 hours. After concentration, treatment with ethanol, and recrystallization as described above, a second crop of product was obtained (0.11 g, 9%, mp 144°–147°). TLC (5% methanol/chloroform, silica): Rf=0.78.

Calc'd for $C_{13}H_{14}N_2O_5S$: N, 9.03, C, 50.31; H, 4.55. Found: N, 9.14, C, 50.45; H, 4.60

Step E
3-N-[2-[5-(Dimethylaminomethyl)-2-furanylmethylthio]ethyl]amino-4-amino-5-benzyloxycarbonylisothiazole-1,1-dioxide ethanolate To a suspension of 3-ethoxy-4-amino-5-benzyloxycarbonylisothiazole-1,1-dioxide (0.43 g, 0.0020 mol) in ethanol (10 ml) there was added a solution of 2-(5-dimethylaminomethyl-2-furanylmethylthio)ethylamine (0.62 g, 0.0020 mol) in ethanol (2 ml). All solids dissolved within 10 minutes and precipitation of a pink solid began after 30 minutes. After 1 hour, the mixture was cooled and the precipitate (0.96 g) filtered off. After three recrystallizations from ethanol, the title product was obtained (0.69 g, 66%, mp 82°–91°). TLC (10% methanol/chloroform, silica): Rf=0.30.

Calc'd for $C_{21}H_{26}H_{10}O_5S_2 \cdot C_2H_5OH$: N, 10.68; C, 52.65; H, 6.18. Found: N, 10.69; C, 52.51; H, 6.12.

EXAMPLE 75
3-[3-[3-(1-Piperidinylmethyl)phenoxy]propylamino]-4-amino-5-carboxyisothiazole-1,1-dioxide A mixture of 3-ethoxy-4-amino-5-t-butyloxycaronylisothiazole-1,1-dioxide (276 mg, 1.0 mmol) and 3-[3-(1-piperidinylmethyl)phenoxyl]propylamine (273 mg, 1.1 mmol) can be heated to about 150° C. for several hours under a nitrogen atmosphere with stirring using an oil bath. The residue can then be washed by trituration with petroleum ether and hexane several times followed by recrystallization of the product.

EXAMPLE 76
3-N-[2-[(4-Methyl-5-imidazolyl)methylthio]ethyl]amino-4-amino-5-ethxycarbonylisothiazole-1,1-dioxide The title compound was obtained from equimolar amounts of the compound of Example 5 and 2-(4-methyl-5-imidazolyl)methylthio]ethylamine according to the procedure of Example 39. The analytically pure material was isolated as a hydrate, mp 116°–119° dec.

EXAMPLE 77
3-N-[2-[5-(Dimethylaminomethyl)-2-furanylmethylthio]ethyl]amino-4-amino-5-t-butyloxycarbonylisothiazole-1,1-dioxide The title compound, a yellow solid, mp 126°–129° dec., was obtained by the procedure of Example 39 using the compound of Example 23 in place of the compound of Example 5.

What is claimed is:
1. Compounds having the formulae:

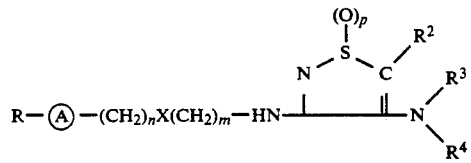

wherein:
R is hydrogen, loweralkyl,

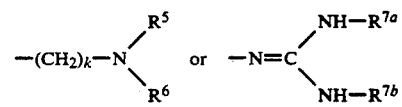

wherein
$R^5$ and $R^6$ are independently hydrogen, loweralkyl, cycloloweralkyl or phenylloweralkyl;
$R^{7a}$ and $R^{7b}$ are independently hydrogen or 3,3,3-trifluoroethyl;
p is 1 or 2;
n is 0 or 1;
m is 2 to 4;
k is 0 to 4;
X is oxygen, sulfur or methylene;
$R^2$ is hydrogen, halogen, loweralkyl, loweralkoxy, aryl, substituted aryl wherein the substituents are loweralkyl, halogen, loweralkoxy, trifluoromethylthio; and trifluoromethylsulfonyl; CH$_2$OH, CN, CONR$^{7a}$R$^3$, or SO$_2$NR$^3$R$^{7a}$ wherein R$^{7a}$ is as defined above and R$^3$ is as defined below; or COR$^9$, CO$_2$R$^9$, CONR$^3$R$^9$SO$_2$R$^9$ wherein R$^9$ is hydrogen, loweralkyl, substituted loweralkyl wherein the substituent is hydroxy, loweralkoxy NHCOR$^{7a}$ wherein R$^{7a}$ is as defined above, aryl or substituted aryl as defined above, and aryloweralkyl;

R$^3$ and R$^4$ are independently hydrogen, loweralkyl, loweralkenyl, loweralkynyl, cycloloweralkyl, phenyl or substituted loweralkyl or substituted loweralkynyl wherein the alkyl and alkynyl substituents are phenyl, substituted phenyl, cycloloweralkyl, imidazolyl, hydroxy, loweralkoxy, loweralkylthio or di(loweralkyl)amino, or NCOR$^3$R$^{7a}$ as defined above;

A is phenylene or, the pharmaceutically acceptable salts and N-oxides thereof.

2. Compounds of claim 1 wherein R$^2$ is hydrogen, carboxy, cyano, loweralkoxy-carbonyl, benzyloxycarbonyl, carbamoyl, substituted carbamoyl, sulfamoyl, loweralkyl, loweralkylsulfonyl, aryl, and substituted aryl.

3. Compounds of claim 2 wherein R$^3$ and R$^4$ are independently hydrogen, loweralkyl, substituted loweralkyl, loweralkynyl, or substituted loweralkynyl wherein the substituents in said alkyl and alkynyl groups are loweralkoxy, phenyl, or imidazolyl.

4. Compounds of claim 3 wherein Ⓐ is m-phenylene; is O; X is oxygen; and m is 3.

5. Compounds of claim 3 wherein A is furyl, imidazolyl, thiazolyl, oxazolyl, thienyl, triazolyl, pyrrolyl, or benzofuranyl.

6. Compounds of claim 1 wherein R-A is 4-methyl-5-imidazolyl, X is sulfur, n is 1, m is 2; and, p is 1 or 2.

7. A compound of claim 1 which is: 3-N-[2-[(4-methyl-5-imidazolyl)methylthio]ethyl]amino-4-amino-5-ethoxycarbonylisothiazole-1,1-dioxide.

8. Compounds of claim 1 wherein X is sulfur, n is 1, m is 2, p is 1 or 2, and R Ⓐ has the formula

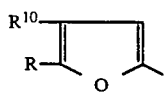

wherein R is CH$_2$NR$^5$R$^6$, and R$^{10}$ is hydrogen, chloro, bromo, loweralkoxycarbonyl, loweralkoxy, loweralkyl, or aryl.

9. A compound of claim 1 which is: 3-N-[2-[5-(dimethylaminomethl-2-furanyl)methylthio]ethyl]amino-4-amino-5-ethoxycarbonylisothiazole-1,1-dioxide.

10. A compound of claim 1 which is: 3-N-[2-[5-(dimethylaminomethyl-2-furanyl)methylthio]ethyl]amino-4-methylamino-5-ethoxycarbonylisothiazole-1,1-dioxide.

11. A compound of claim 1 which is: 3-N-[2-[5-(dimethylaminomethyl-2-furanyl)methylthio]ethyl]amino-4-amino-5-benzyloxycarbonylisothiazole-1,1-dioxide.

12. A compound of claim 1 which is: 3-N-[2-[5-(dimethylaminomethyl-2-furanyl)methylthio]ethyl]amino-4-amino-5-methanesulfonylisothiazole-1,1-dioxide.

13. A compound of claim 1 which is: 3-N-[2-[5-(dimethylaminomethyl-2-furanyl)methylthio]ethyl]amino-4-amino-5-carboxylisothiazole-1,1-dioxide.

14. A compound of claim 1 which is: 3-N-[2-[5-(dimethylaminomethyl-2-furanyl)methylthio]ethyl]amino-4-amino-5-carbamoylisothiazole-1-oxide.

15. A compound of claim 1 which is: 3-N-[2-[5-(dimethylaminomethyl-2-furanyl)methylthio]ethyl]amino-4-amino-5-ethoxycarbonylisothiazole-1oxide.

16. A compound of claim 1 which is: 3-N-[2-[5-(dimethylaminomethyl-2-furanyl)methylthio]ethyl]amino-4-amino-5-benzyloxycarbonylisothiazole-1-oxide.

17. A compound of claim 1 which is: 3-N-[2-[5-dimethylaminomethyl-2-furanyl)methylthio]ethyl]amino-4-amino-5-methanesulfonylisothiazole-1-oxide.

18. A compound of claim 1 which is: 3-N-[2-[5-(dimethylaminomethyl-2-furanyl)methylthio]ethyl]amino-4-amino-5-cyanoisothiazole-1,1-dioxide.

19. A compound of claim 1 which is: 3-N-[2-[5-(dimethylaminomethyl-2-furanyl)methylthio]ethyl]amino-4-amino-5-N,N-dimethylcarbamoylisothiazole-1,1-dioxide.

20. A compound of claim 1 which is: 3-N-[2-[5-(dimethylaminomethyl-2-furanyl)methylthio]ethyl]amino-4-amino-5-sulfamoylisothiazole-1,1-dioxide.

21. A compound of claim 1 which is: 3-N-[2-[5-(dimethylaminomethyl-2-furanyl)methylthio]ethyl]amino-4-amino-5-(2-hydroxyethoxy)carbonylisothiazole-1,1-dioxide.

22. A compound of claim 1 which is: 3-N-[2-[5-(dimethylaminomethyl-2-furanyl)methylthio]ethyl]amino-4-amino-5-(2-acetamidoethoxy)carbonylisothiazole-1,1-dioxide.

23. A compound of claim 1 which is: 3-N-[2-[5-(dimethylaminomethyl-2-furanyl)methylthio]ethyl]amino-4-amino-5-t-butyloxycarbonylisothiazole-1,1-dioxide.

24. Compounds of claim 1 wherein X is sulfur, n is 1, m is 2, p is 1 or 2, and R Ⓐ has the formula

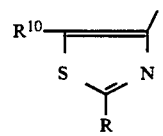

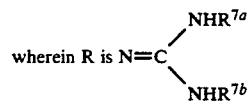

wherein R$^{7a}$ and R$^{7b}$ are independently hydrogen, loweralkyl, or CF$_3$CH$_2$; and R$^{10}$ is hydrogen, chloro, bromo, loweralkoxycarbonyl, loweralkoxy, loweralkyl, or aryl.

25. A compound of claim 24 which is: 3-N-[2-[(2-guanidino-4-thiazolyl)methylthio]ethyl]amino-4-amino-5-ethoxycarbonylisothiazole-1,1-dioxide.

26. A compound of claim 24 which is: 3-N-[2-[(2-guanidino-5-methyl-4-thiazolyl)methylthio]ethyl]amino-4-amino-5-sulfamoylisothiazole-1,1-dioxide.

27. A compound of claim 24 which is: 3-N-[2-[(2-guanidino-5-chloro-4-thiazolyl)methylthio]ethyl]amino-4-amino-5-ethoxycarbonylisothiazole-1,1-dioxide.

28. Compounds of claim 1 wherein X is oxygen, n is 0, m is 3, p is 1 or 2, and R A has the formula

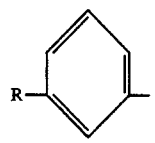

29. A compound of claim 28 wherein R is —CH$_2$NR$^5$R$^6$ wherein R$^5$ and R$^6$ are independently hydrogen, loweralkyl or cycloloweralkyl.

30. Compounds having the formulae:

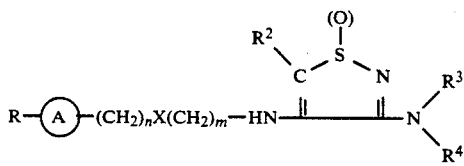

wherein: R is hydrogen, loweralkyl,

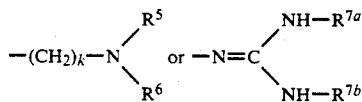

wherein:

R$^5$ and R$^6$ are independently hydrogen, loweralkyl, cycloloweralkyl or phenylloweralkyl R$^{7a}$ and R$^{7b}$ are independently hydrogen or 3,3,3-trifluoroethyl;

p is 1 or 2;

n is 0 or 1;
m is 2 to 4;
k is 0 to 4;
X is oxygen, sulfur or methylene;
R$^2$ is hydrogen, halogen, loweralkyl, loweralkoxy, aryl, substituted aryl wherein the substituents are loweralkyl, halogen, loweralkoxy, trifluoromethylthio, and trifluoromethylsulfonyl; CH$_2$OH, CN, CONR$^{7a}$R$^3$, or SO$_2$NR$^3$R$^{7a}$ wherein R$^{7a}$ is as defined above and R$^3$ is as defined below; or COR$^9$, CO$_2$R$^9$, CONR$^3$R$^9$ and SO$_2$R$^9$ wherein R$^9$ is hydrogen, loweralkyl, substituted loweralkoxy, NHCOR$^{7a}$ wherein R$^{7a}$ is as defined above, aryl or substituted aryl as defined above, and aryloweralkyl;

R$^3$ and R$^4$ are independently hydrogen, loweralkyl, loweralkenyl, loweralkynyl, cycloloweralkyl, phenyl or substituted loweralkyl or substituted loweralkynyl wherein the alkyl and alkynyl substituents are phenyl, substituted phenyl, cycloloweralkyl, imidazolyl, morpholino, hydroxy, loweralkoxy, loweralkylthio, di(loweralkyl) amino, or NCOR$^3$R$^{7a}$ as defined above A is phenylene or the pharmaceutically acceptable salts and N-oxides thereof.

31. A pharmaceutical composition useful in the treatment of gastric secretion in a mammal, comprising a pharmaceutically effective amount of a compound of claim 1 and a pharmaceutically acceptable carrier.

32. A method useful in the treatment of gastric secretion in a mammal, which comprises administering to a mammal in need thereof a pharmaceutically effective amount of a compound of claim 1.

* * * * *